US011028452B2

(12) United States Patent
Harder et al.

(10) Patent No.: US 11,028,452 B2
(45) Date of Patent: Jun. 8, 2021

(54) ASSAY FOR THE DIAGNOSIS OF DERMATOPHYTOSIS

(71) Applicant: EUROIMMUN MEDIZINISCHE LABORDIAGNOSTIKA AG, Luebeck (DE)

(72) Inventors: Melanie Harder, Kiel (DE); Yvonne Graeser, Hangelsberg (DE); Christiane Kupsch, Berlin (DE); Markus Cavalar, Herrnburg (DE)

(73) Assignee: EUROIMMUN Medizinische Labordiagnostika AG, Luebeck (DE)

( * ) Notice: Subject to any disclaimer, the term of this patent is extended or adjusted under 35 U.S.C. 154(b) by 0 days.

(21) Appl. No.: 15/938,890

(22) Filed: Mar. 28, 2018

(65) Prior Publication Data
US 2018/0291472 A1 Oct. 11, 2018

(30) Foreign Application Priority Data
Mar. 30, 2017 (EP) .................................... 17000524

(51) Int. Cl.
*C12Q 1/6895* (2018.01)
*C12Q 1/6851* (2018.01)
*C12Q 1/04* (2006.01)

(52) U.S. Cl.
CPC ............. *C12Q 1/6895* (2013.01); *C12Q 1/04* (2013.01); *C12Q 1/6851* (2013.01)

(58) Field of Classification Search
None
See application file for complete search history.

(56) References Cited

U.S. PATENT DOCUMENTS

| 6,399,364 B1 * | 6/2002 | Reeve | C12Q 1/6874 435/287.1 |
| 6,582,908 B2 * | 6/2003 | Fodor | B01J 19/0046 435/288.3 |
| 2010/0143916 A1 * | 6/2010 | Liew | C12N 15/113 435/6.14 |
| 2010/0311041 A1 | 12/2010 | Brillowska-Dabrowska | |

FOREIGN PATENT DOCUMENTS

| WO | 01/86003 A2 | 11/2001 |
| WO | 2007/106407 A2 | 9/2007 |

OTHER PUBLICATIONS

Sakai et al Mycophatologica. 2014. 178: 11-26.*
Kawaoka et al (Insect Biochem Molec Biology. 2008. 38: 1058-1065 (Year: 2008).*
NCBI Database Gen Bank Accession No. AB419215.1. Mar. 11, 2009. Available via URL: <ncbi.nlm.nih.gov/nuccore/AB419215.1/> (Year: 2009).*
Liu et al Nucleic acids Research. 2006. 34(1): e4, pp. 1-8 (Year: 2006).*
Gräser et al., "Diagnostic PCR of dermatophytes—an overview," *JDDG: Journal der Deutschen Dermatologischen Gesellschaft* 10(10):721-725, 2012.
Gräser et al., "New insights in dermatophyte research," *Medical Mycology* 56(S1):S2-S9, 2018.
Gräser et al., "The New Species Concept in Dermatophytes—a Polyphasic Approach," *Mycopathologia* 166(5,6):239-256, 2008.
Hameed et al., "*Trichophyton verrucosum* infection in livestock in the Chitral district of Pakistan," *J Infect Dev Ctries* 11(4):326-333, 2017.
Jin, "EST030134 Trichophyton rubrum cDNA library 7 Trichophyton rubrum cDNA clone plasmid:FUNGI_9_110B_31, mRNA sequence," XP-002774268, retrieved from EBI accession No. EM_EST:DW706653, Nov. 14, 2006, 1 page.
Jung et al., "Identification of Dermatophytes by Polymerase Chain Reaction-Restriction Fragment Length Polymorphism Analysis of Metalloproteinase-1," *Ann Dermatol* 26(3):338-342, 2014.
Kupsch et al., "The agony of choice in dermatophyte diagnostics—performance of different molecular tests and culture in the detection of *Trichophyton rubrum* and *Trichophyton interdigitale*," *Clinical Microbiology and Infection* 22:735.e11-735.e17, 2016.
Kupsch et al., "Dermatophytes and guinea pigs—an underestimated danger?," *Hautarzt* 68:827-830, 2017 (with English translation, 11 pages).
Martinez et al., "Comparative Genome Analysis of *Trichophyton rubrum* and Related Dermatophytes Reveals Candidate Genes Involved in Infection," *MBio* 3(5):e00259-12, 2012 (14 pages).
Mirhendi et al., "Translation elongation factor 1-α gene as a potential taxonomic and identification marker in dermatophytes," *Medical Mycology* 53(3):215-224, 2015.
Ohst et al., "Detection of common dermatophytes in clinical specimens using a simple quantitative real-time TaqMan polymerase chain reaction assay," *British Journal of Dermatology* 174:602-609, 2016.
Penn et al., "Human genome-derived single exon probe ORF from lung SEQ ID No. 18528," XP-002774266, retrieved from EBI accession No. GSN:ABS18537, Aug. 19, 2002, 1 page.
Rezaei-Matehkolaei et al., "Nucleotide sequence analysis of beta tubulin gene in a wide range of dermatophytes," *Medical Mycology* 52(7):674-688, 2014.

(Continued)

*Primary Examiner* — Carla J Myers
(74) *Attorney, Agent, or Firm* — Grüneberg and Myers PLLC

(57) ABSTRACT

The present invention relates to a primer pair comprising a forward primer and a reverse primer for amplifying a nucleic acid from a pathogen associated with a skin, hair and nail infection comprising SEQ ID NO:22, a nucleic acid capable of hybridizing specifically to a nucleic acid sequence from a pathogen associated with a skin, hair and nail infection comprising SEQ ID NO:22, a carrier comprising the nucleic acid, a method comprising the step detecting in a sample a nucleic acid sequence comprising SEQ ID NO:22 from a pathogen associated with a skin, hair and nail infection, a use of the primer pair, the nucleic acid or the carrier for the diagnosis of a disease and a kit comprising the primer pair, the nucleic acid and/or the carrier for the diagnosis of a disease.

18 Claims, 7 Drawing Sheets
Specification includes a Sequence Listing.

(56) References Cited

OTHER PUBLICATIONS

Sybren de Hoog et al., "Toward a Novel Multilocus Phylogenetic Taxonomy for the Dermatophytes," *Mycopathologia 182*:5-31, 2017.
Wang et al., "Analysis of the dermatophyte *Trichophyton rubrum* expressed sequence tags," *BMC Genomics 7*:255, 2006 (13 pages).
European Office Action dated Aug. 1, 2019, corresponding EP application No. 18 163 653.1 (5 pages).
Office Action dated Nov. 5, 2019 in European Application No. 18163653.1, 5 pages.
*Tricophyton benhamiae* white genome sequence from NCBI datasets available at URL:https://www.ncbi.nlm.nih.gov/assembly/GCF_000151125.1/, submitted Mar. 17, 2010 by Arthroderma Genome Sequencing Consortium, obtained May 4, 2020.
*Trichophyton tonsurans* genome sequence from NCBI datasets available at URL:https://www.ncbi.nlm.nih.gov/assembly/GCA_000151455.1/, submitted Aug. 11, 2009 by Broad Institute, obtained May 4, 2020.
*Trichophyton equinum* genome sequence from NCBI datasets available at URL:https://www.ncbi.nlm.nih.gov/assembly/GCA_000151175.1/, submitted Oct. 22, 2008 by Broad Institute, obtained May 4, 2020.
*Trichophyton interdigitale* genome sequence from NCBI datasets available at URL:https://www.ncbi.nlm.nih.gov/assembly/GCA_000622975.1/, submitted Apr. 2, 2014 by Broad Institute, obtained May 4, 2020.
Office Action dated Feb. 25, 2020 in Indian Application No. 201834009101, bilingual, with English, 7 pages.
Canadian Office Action dated Apr. 15, 2020 in Canadian Application No. 2,999,712, 9 pages.
European Office Action dated Apr. 28, 2020 in European Application No. 18 163 653.1, 5 pages.
Singaporean Written Opinion dated Apr. 30, 2020 in Singaporean Application No. 10201802281X, 7 pages.
GenBank Accession No. ABS18537, "cytochrome oxidase subunit I, partial (mitochondrion) [Synergus diaphanous]," Jul. 23, 2016, https://www.ncbi.nlm.nih.gov/protein/ABS18537, 2 pages.
GenBank Accession No. ATH86636, "transcriptional regulator [Brochothrix thermosphacta]," Oct. 4, 2017, https://www.ncbi.nlm.nih.gov/protein/ATH86636, 2 pages.
Office Action dated Aug. 4, 2020 in Japanese Application No. 2018-062538 with English translation, 15 pages.
Examination Report No. 1 dated Aug. 18, 2020 in Australian Application No. 2018202209, 9 pages.
Biomers.net Oligonucleotides, "Reverse Linkers"; downloaded Oct. 5, 2020 from URL: https://www.biomers.net/en/products/dna/reactive_linker.html?lang=en, 18 pages.
Todt et al., DNA Microarrays for Biomedical research: Methods and Protocols; 2009, 529:81-100.
Examination Report No. 2 dated Nov. 24, 2020 in Australian Application No. 2018202209, 4 pages.

\* cited by examiner

```
T.interdigitale          ---------------------CACGGTAATAACCGTACCCGAGGTCCCCGGCGTGCGGA
T.tonsurans              ---------------------CACGCTTATAACCGTACCCGAGATCCTTGGCGTACGGA
T.benhamiae(white)       CTCTGGTGAGAGAGTGCAGTTGCACGATTGTAACCATACCCATGGTCCTTGCAGTGCGGT
T.erinacei               CTCCCGTGAGAGAGTGCAGTTGCACTACTGTAACCGTACCCATGGTCCTTGCAGTGTGGG
T.benhamiae(African)     CTCTTGTGAGAGAGTGCAGTTGCACGCTGATAACCGTACCCATGGTCCTTGCAGTGCGGC
T.equinum                ---------------------CACGCTCATAACCGTACCCGAGATCCCTGGCGTGCGGA
T.benhamiae(yellow)      CTCCGGTGAGAGAGTGCAATTGCACGATCGTAACCGTACCCCAAGTCCTTGCAGAACGGT
T.concentricum           CTCCGGTGAGAGAGTGCAGTTGCACGATTGTAACCGTACCCCAAGTCCTTGCAGAACGGT
                                              ***     .*****.*****  :...***   *  .*:.  **
consensus                xxxxxxxxxxxxxxxxxxxxxxCACXXXXXTAACCXTACCCxxxxTCCxxGxxGxxxGGx T.interdigitale          CTCATAACGGCTGGATTATGGGCTCCTTCGTGGATTATGGTCGAGACGCGATCTTGACCA
T.tonsurans              TGCATAACGGCTGGATTATGGGCTCCTTCGTGGATTATGGTCGAGACGCGATCTTGATGA
T.benhamiae(white)       GTGACAGCATTTGGATTATGGGCTCCTTCGTGGATTACGGTCCCGACACGATCCTGACGA
T.erinacei               TTAGCAACATTTGGATTATGGAGTGCTTCGTGGATTACGGTCCCAACACGATCCTGACCA
T.benhamiae(African)     TTGACAACACTTGGATTATGGGCTCCTTCGTGGACTACGGTCCCGATACGATCCTGACGA
T.equinum                CGCATAACGGCTGGATTATGGGCTCCTTCGTGGATTATGGTCGAGACGCGATCTTGATGA
T.benhamiae(yellow)      GTAACAACCCTTGGATTATGGAGTAATTCGTGGATTATGGTGTCGACACGATCCTGGCCA
T.concentricum           GTAACAACACTTGGATTATGGAGTAATTCGTGGATTATGGTGTCGACACGATCCTGGCCA
                          .*.*   *********. * .******** ** *** ..* .***** **.  *
consensus                xxxxxAxCxxxTGGATTATGGxxTxxTTCGTGGAxTAxGGTxxxxAxxCGATCxTGxxxA T.interdigitale          TGGCACTTCTTGGTGAGATGGGGCAGTTGCCAAAAGATGTCGCAGGGAAAGACCGAATTC
T.tonsurans              TGGCACTTATCGGTGAGATGAGGCAGTTGCCAAAAGATGTTGCAGGGGAAGACCGAATTC
T.benhamiae(white)       TGGCACTCATTGGTGCGGTGGGGCAGTTGCCAAAAGAGGGAGCAGGGGTGAACCTCATTC
T.erinacei               TGGCACTTCTTGGTTTTGTGCGCCATATTCCAAAAGATGGGGCAGGGGTGAACCTCATTG
T.benhamiae(African)     TGGCACTTATTGGTGCGGTGGGGCAGTTGCCAAAAGATGTCGCAGGGGTGAACCTCATTC
T.equinum                TGGCACTTATCGGTGAGATGAGGCAGTTGCCAAAAGATGTAGCAGGGGAAGACCGAATTC
T.benhamiae(yellow)      TGGCACTTATTGGTTTGGTGGGGCAGTTGCCAAAAGATGGAGCAGGGGAAGACCGAGTTC
T.concentricum           TGGCACTTATTGGTTTGGTGGGGCAGTTGCCAAAAGTTGGGGCAGGGGAAGACCGAGTTC
                         *******  .* ***    .** *  **  :*  *******; *  ****** :..***  ...**
consensus                TGGCACTxxTxGGTxxxxTGxGxCAxxTxCCAAAAGxxGxxGCAGGGxxxxACCxxxTTx T.interdigitale          ATGGCTGGGAGGGTGTAGGCAATAGTTCTGCGACGGCATCGTCGATGTTTATCGTGGCAG
T.tonsurans              ATGGCTGGGAGGGTGTAGGCAATAGTTCTGGGACGGCATCGTCGATGTTTATCGTAGCAG
T.benhamiae(white)       CTAGCTGGAAAGGTGTAGGCAATGGTTCTGGGACTGCATCGGCGAGGACCATCGGAGCAG
T.erinacei               TTAGATGGAAGGGTGTAGGCAATGGTTCTGGGACCGCATCGGCGAGGACCATCGGAGCAG
T.benhamiae(African)     CTAGATGGAAAGGTGTAGGCAATGGTTCTGGGACCGCATCGGCGAGGACCATCGGAGCAG
T.equinum                ATGGCTGGGAGGGTGTAGGCAATAGTTCTGGGACGGCATCGTCGATGTTTATCGTAGCAG
T.benhamiae(yellow)      TCGCCTGGAAGGGTGTAGGCAATGATTTTGGGCCTACATCGGTGACGTGCATCGGAGCAG
T.concentricum           TCGCCTGGAAGGGTGTAGGCAATGGTTCTGGGCCTACATCGGTGACGTGCATCGGAGTAG
                          .***.*.*************..**  ** *.* *****  ** **.;  ****  .* **
consensus                xxxxxTGGxAxGGTGTAGGCAATxxTTxTGxGxCxxCATCGxxGAxGxxxATCGxxGxAG T.interdigitale          AACCACTTAACAGGGCCACCCTCTGAAACGGATGCTTTGGAAATCGAGTTGAGATGCGCG
T.tonsurans              AACCACTGAACAGGGCCACCCTCTGAAACGGATGCTTTGGAAATCGAGTAGAGATGCATG
T.benhamiae(white)       AAC---------------------------------------------------------
T.erinacei               TA----------------------------------------------------------
T.benhamiae(African)     AAC---------------------------------------------------------
T.equinum                AACCACTGAACAGGGCCACCCTCTGGAACGGATGCTTTGGAAATCGAGTAGAGATGCATG
T.benhamiae(yellow)      TAC---------------------------------------------------------
T.concentricum           TAC---------------------------------------------------------
                         :*
consensus                xA T.interdigitale          GAAACCTCCTTCCTGGTTGCAGGATC
T.tonsurans              GAAACCTCCTTCCTGGTTGCAGAATC
T.benhamiae(white)       --------------------------
T.erinacei               --------------------------
T.benhamiae(African)     --------------------------
T.equinum                GAAACCTCCTTCCTGGTTGCAGAATC
T.benhamiae(yellow)      --------------------------
T.concentricum           --------------------------
```

Fig. 1

FIG. 3A
Trichophyton benhamiae (yellow)
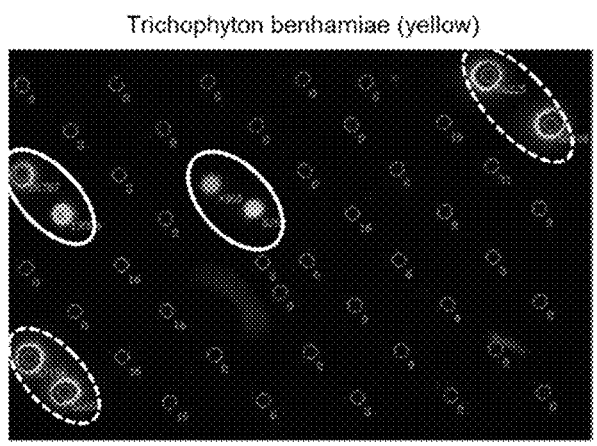
FIG. 3B
Trichophyton benhamiae (white)
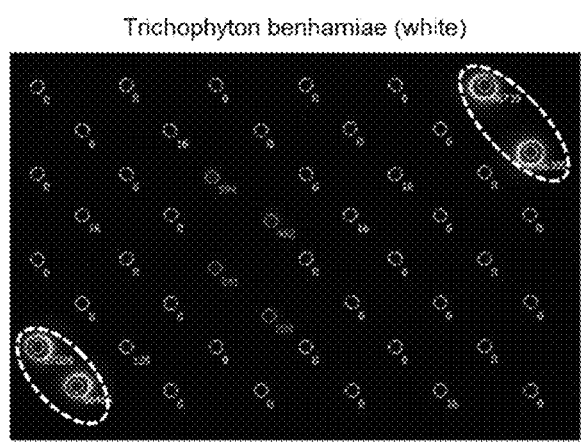
Trichophyton benhamiae (african)
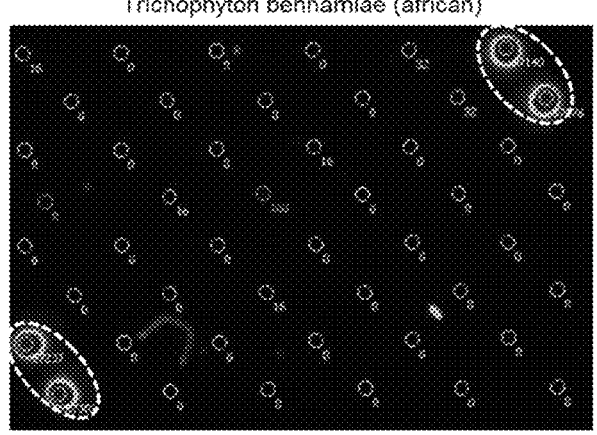
Trichophyton concentricum
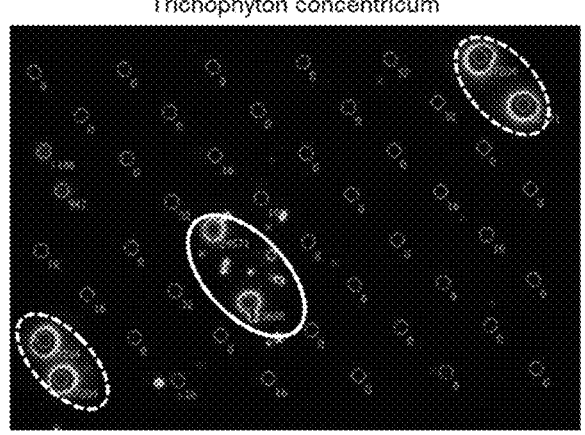
FIG. 3C
FIG. 3D FIG. 4A
Trichophyton benhamiae (white)
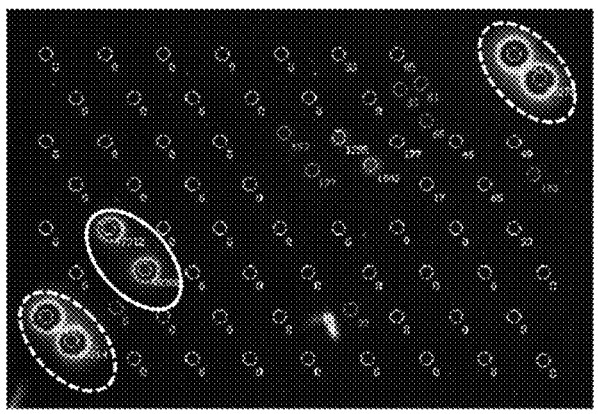
FIG. 4B
Trichophyton benhamiae (yellow)
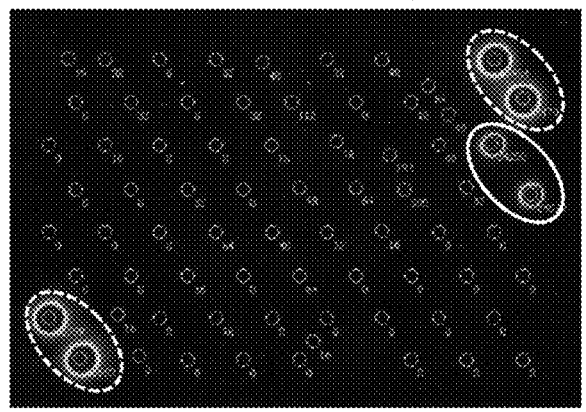
Trichophyton benhamiae (african)
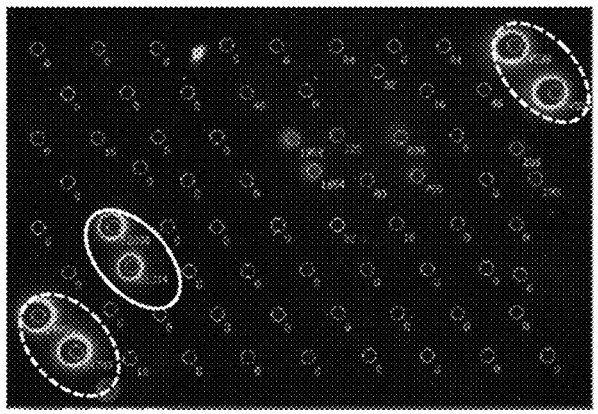
FIG. 4C

SEQUENCE LISTING

<160> NUMBER OF SEQ ID NOS: 30

<210> SEQ ID NO 1
<211> LENGTH: 220
<212> TYPE: DNA
<213> ORGANISM: Artificial Sequence
<220> FEATURE:
<223> OTHER INFORMATION: Consensus sequence of nucleic acid to be
      amplified
<220> FEATURE:
<221> NAME/KEY: misc_feature
<222> LOCATION: (4)..(8)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (20)..(23)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature

```
<222> LOCATION: (33)..(35)
<223> OTHER INFORMATION: n is a, c, g, or t
<220> FEATURE:
<221> NAME/KEY: misc_feature
<222> LOCATION: (38)..(43)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (47)..(49)
<223> OTHER INFORMATION: n is a, c, g, or t
<220> FEATURE:
<221> NAME/KEY: misc_feature
<222> LOCATION: (60)..(61)
<223> OTHER INFORMATION: n is a, c, g, or t
<220> FEATURE:
<221> NAME/KEY: misc_feature
<222> LOCATION: (63)..(64)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (80)..(83)
<223> OTHER INFORMATION: n is a, c, g, or t
<220> FEATURE:
<221> NAME/KEY: misc_feature
<222> LOCATION: (85)..(86)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (95)..(97)
<223> OTHER INFORMATION: n is a, c, g, or t
<220> FEATURE:
<221> NAME/KEY: misc_feature
<222> LOCATION: (106)..(107)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (113)..(116)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t
<220> FEATURE:
<221> NAME/KEY: misc_feature
<222> LOCATION: (124)..(125)
<223> OTHER INFORMATION: n is a, c, g, or t
<220> FEATURE:
<221> NAME/KEY: misc_feature
<222> LOCATION: (127)..(127)
<223> OTHER INFORMATION: n is a, c, g, or t
<220> FEATURE:
<221> NAME/KEY: misc_feature
<222> LOCATION: (135)..(136)
<223> OTHER INFORMATION: n is a, c, g, or t
<220> FEATURE:
```

```
<221> NAME/KEY: misc_feature
<222> LOCATION: (138)..(139)
<223> OTHER INFORMATION: n is a, c, g, or t
<220> FEATURE:
<221> NAME/KEY: misc_feature
<222> LOCATION: (146)..(149)
<223> OTHER INFORMATION: n is a, c, g, or t
<220> FEATURE:
<221> NAME/KEY: misc_feature
<222> LOCATION: (153)..(155)
<223> OTHER INFORMATION: n is a, c, g, or t
<220> FEATURE:
<221> NAME/KEY: misc_feature
<222> LOCATION: (158)..(163)
<223> OTHER INFORMATION: n is a, c, g, or t
<220> FEATURE:
<221> NAME/KEY: misc_feature
<222> LOCATION: (167)..(167)
<223> OTHER INFORMATION: n is a, c, g, or t
<220> FEATURE:
<221> NAME/KEY: misc_feature
<222> LOCATION: (169)..(169)
<223> OTHER INFORMATION: n is a, c, g, or t
<220> FEATURE:
<221> NAME/KEY: misc_feature
<222> LOCATION: (182)..(183)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (191)..(191)
<223> OTHER INFORMATION: n is a, c, g, or t
<220> FEATURE:
<221> NAME/KEY: misc_feature
<222> LOCATION: (193)..(194)
<223> OTHER INFORMATION: n is a, c, g, or t
<220> FEATURE:
<221> NAME/KEY: misc_feature
<222> LOCATION: (200)..(201)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (206)..(208)
<223> OTHER INFORMATION: n is a, c, g, or t
<220> FEATURE:
<221> NAME/KEY: misc_feature
<222> LOCATION: (213)..(214)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (219)..(219)
<223> OTHER INFORMATION: n is a, c, g, or t

<400> SEQUENCE: 1
cacnnnnnta accntacccn nnntccnngn ngnnnggnnn nnnancnnnt ggattatggn      60
ntnnttcgtg gantanggtn nnnanncgat cntgnnnatg gcactnntng gtnnnntgng    120
ncanntncca aaagnngnng cagggnnnna ccnnnttnnn nnntggnang gtgtaggcaa    180
tnnttntgng ncnncatcgn ngangnnnat cgnngnagna                         220
```

```
<210> SEQ ID NO 2
<211> LENGTH: 304
<212> TYPE: DNA
<213> ORGANISM: Artificial Sequence
<220> FEATURE:
<223> OTHER INFORMATION: Target sequence from T. tonsurans

<400> SEQUENCE: 2
cacgcttata accgtacccg agatccttgg cgtacggatg cataacggct ggattatggg    60
ctccttcgtg gattatggtc gagacgcgat cttgatgatg gcacttatcg gtgagatgag   120
gcagttgcca aaagatgttg caggggaaga ccgaattcat ggctgggagg gtgtaggcaa   180
tagttctggg acggcatcgt cgatgtttat cgtagcagaa ccactgaaca gggccaccct   240
ctgaaacgga tgctttggaa atcgagtaga gatgcatgga aacctccttc ctggttgcag   300
aatc                                                                304

<210> SEQ ID NO 3
<211> LENGTH: 304
<212> TYPE: DNA
<213> ORGANISM: Artificial Sequence
<220> FEATURE:
<223> OTHER INFORMATION: Target sequence from T. equinum

<400> SEQUENCE: 3
cacgctcata accgtacccg agatccctgg cgtgcggacg cataacggct ggattatggg    60
ctccttcgtg gattatggtc gagacgcgat cttgatgatg gcacttatcg gtgagatgag   120
gcagttgcca aaagatgtag caggggaaga ccgaattcat ggctgggagg gtgtaggcaa   180
tagttctggg acggcatcgt cgatgtttat cgtagcagaa ccactgaaca gggccaccct   240
ctggaacgga tgctttggaa atcgagtaga gatgcatgga aacctccttc ctggttgcag   300
aatc                                                                304

<210> SEQ ID NO 4
<211> LENGTH: 304
<212> TYPE: DNA
<213> ORGANISM: Artificial Sequence
<220> FEATURE:
<223> OTHER INFORMATION: Target sequence from T. interdigitale
       (anthrophilic + zoophilic), I, II, II, III*, IV, M

<400> SEQUENCE: 4
cacggtaata accgtacccg aggtccccgg cgtgcggact cataacggct ggattatggg    60
ctccttcgtg gattatggtc gagacgcgat cttgaccatg gcacttcttg gtgagatggg   120
gcagttgcca aaagatgtcg cagggaaaga ccgaattcat ggctgggagg gtgtaggcaa   180
tagttctgcg acggcatcgt cgatgtttat cgtggcagaa ccacttaaca gggccaccct   240
ctgaaacgga tgctttggaa atcgagttga gatgcgcgga aacctccttc ctggttgcag   300
gatc                                                                304

<210> SEQ ID NO 5
<211> LENGTH: 243
<212> TYPE: DNA
<213> ORGANISM: Artificial Sequence
<220> FEATURE:
<223> OTHER INFORMATION: Target sequence from T. benhamiae (yellow)

<400> SEQUENCE: 5
ctccggtgag agagtgcaat tgcacgatcg taaccgtacc ccaagtcctt gcagaacggt    60
gtaacaaccc ttggattatg gagtaattcg tggattatgg tgtcgacacg atcctggcca   120
```

```
tggcacttat tggtttggtg gggcagttgc caaaagatgg agcagggaa gaccgagttc      180 tcgcctggaa gggtgtaggc aatgattttg ggcctacatc ggtgacgtgc atcggagcag      240
tac                                                                   243
```

<210> SEQ ID NO 6
<211> LENGTH: 243
<212> TYPE: DNA
<213> ORGANISM: Artificial Sequence
<220> FEATURE:
<223> OTHER INFORMATION: Target sequence from T. benhamiae (white)

<400> SEQUENCE: 6

```
ctctggtgag agagtgcagt tgcacgattg taaccatacc catggtcctt gcagtgcggt      60
gtgacagcat ttggattatg ggctccttcg tggattacgg tcccgacacg atcctgacga      120
tggcactcat tggtgcggtg gggcagttgc caaaagaggg agcagggtg aacctcattc       180 ctagctggaa aggtgtaggc aatggttctg ggactgcatc ggcgaggacc atcggagcag      240
aac                                                                   243
```

<210> SEQ ID NO 7
<211> LENGTH: 243
<212> TYPE: DNA
<213> ORGANISM: Artificial Sequence
<220> FEATURE:
<223> OTHER INFORMATION: T. benhamiae (African)

<400> SEQUENCE: 7

```
ctcttgtgag agagtgcagt tgcacgctga taaccgtacc catggtcctt gcagtgcggc      60
ttgacaacac ttggattatg ggctccttcg tggactacgg tcccgatacg atcctgacga      120
tggcacttat tggtgcggtg gggcagttgc caaaagatgt cgcagggtg aacctcattc       180 ctagatggaa aggtgtaggc aatggttctg ggaccgcatc ggcgaggacc atcggagcag      240
aac                                                                   243
```

<210> SEQ ID NO 8
<211> LENGTH: 243
<212> TYPE: DNA
<213> ORGANISM: Artificial Sequence
<220> FEATURE:
<223> OTHER INFORMATION: Target sequence from T. concentricum

<400> SEQUENCE: 8

```
ctccggtgag agagtgcagt tgcacgattg taaccgtacc ccaagtcctt gcagaacggt      60
gtaacaacac ttggattatg gagtaattcg tggattatgg tgtcgacacg atcctggcca      120
tggcacttat tggtttggtg gggcagttgc caaaagttgg ggcaggggaa gaccgagttc      180
tcgcctggaa gggtgtaggc aatggttctg ggcctacatc ggtgacgtgc atcggagtag      240
tac                                                                   243
```

<210> SEQ ID NO 9
<211> LENGTH: 242
<212> TYPE: DNA
<213> ORGANISM: Artificial Sequence
<220> FEATURE:
<223> OTHER INFORMATION: Target sequence from T. erinacei

<400> SEQUENCE: 9

```
ctcccgtgag agagtgcagt tgcactactg taaccgtacc catggtcctt gcagtgtggg      60
```

-continued

```
ttagcaacat ttggattatg gagtgcttcg tggattacgg tcccaacacg atcctgacca      120
tggcacttct tggttttgtg cgccatattc caaaagatgg ggcaggggtg aacctcattg      180
ttagatggaa gggtgtaggc aatggttctg ggaccgcatc ggcgaggacc atcggagcag      240
ta                                                                      242
```

```
<210> SEQ ID NO 10
<211> LENGTH: 17
<212> TYPE: DNA
<213> ORGANISM: Artificial Sequence
<220> FEATURE:
<223> OTHER INFORMATION: Universal forward primer (Trichophyton
      tonsurans, Trichophyten equinum, Trichophyton interdigitale
      (antrophilic + zoophilic) I, II, III, III*, IV, M)

<400> SEQUENCE: 10
gggagggaga ctagttg                                                      17

<210> SEQ ID NO 11
<211> LENGTH: 15
<212> TYPE: DNA
<213> ORGANISM: Artificial Sequence
<220> FEATURE:
<223> OTHER INFORMATION: Universal forward primer (Trichophyton
      benhamiae (yellow), Trichophyton benhamiae (white), Trichophyton
      benhamiae (African), Trichophyton concentricum, Trichophyton
      erinacei)

<400> SEQUENCE: 11
gcatttccca tggct                                                        15

<210> SEQ ID NO 12
<211> LENGTH: 17
<212> TYPE: DNA
<213> ORGANISM: Artificial Sequence
<220> FEATURE:
<223> OTHER INFORMATION: Universal reverse primer (Trichophyton
      tonsurans, Trichophyten equinum, Trichophyton interdigitale
      (antrophilic + zoophilic) I, II, III, III*, IV, M)

<400> SEQUENCE: 12
aatttttcgc cgccaag                                                      17

<210> SEQ ID NO 13
<211> LENGTH: 15
<212> TYPE: DNA
<213> ORGANISM: Artificial Sequence
<220> FEATURE:
<223> OTHER INFORMATION: Universal reverse primer (Trichophyton
      benhamiae (yellow), Trichophyton benhamiae (white), Trichophyton
      benhamiae (African), Trichophyton bullosum, Trichophyton
      concentricum, Trichophyton erinacei)

<400> SEQUENCE: 13
tggctctgtt acgtg                                                        15

<210> SEQ ID NO 14
<211> LENGTH: 23
<212> TYPE: DNA
<213> ORGANISM: Artificial Sequence
<220> FEATURE:
<223> OTHER INFORMATION: Trichophyton tonsurans probe

<400> SEQUENCE: 14
gatccttggc gtacggatgc ata                                               23
```

```
<210> SEQ ID NO 15
<211> LENGTH: 16
<212> TYPE: DNA
<213> ORGANISM: Artificial Sequence
<220> FEATURE:
<223> OTHER INFORMATION: Trichophyten equinum probe

<400> SEQUENCE: 15
agatccctgg cgtgcg                                              16

<210> SEQ ID NO 16
<211> LENGTH: 18
<212> TYPE: DNA
<213> ORGANISM: Artificial Sequence
<220> FEATURE:
<223> OTHER INFORMATION: Trichophyton interdigitale (antrophilic +
      zoophilic) I, II, III, III*, IV, M probe

<400> SEQUENCE: 16
gagatgcgcg gaaacctc                                            18

<210> SEQ ID NO 17
<211> LENGTH: 27
<212> TYPE: DNA
<213> ORGANISM: Artificial Sequence
<220> FEATURE:
<223> OTHER INFORMATION: Trichophyton benhamiae (yellow) probe

<400> SEQUENCE: 17
gtgtaggcaa tgattttggg cctacat                                  27

<210> SEQ ID NO 18
<211> LENGTH: 25
<212> TYPE: DNA
<213> ORGANISM: Artificial Sequence
<220> FEATURE:
<223> OTHER INFORMATION: Trichophyton benhamiae (white) probe

<400> SEQUENCE: 18
tgcagtgcgg tgtgacagca tttgg                                    25

<210> SEQ ID NO 19
<211> LENGTH: 19
<212> TYPE: DNA
<213> ORGANISM: Artificial Sequence
<220> FEATURE:
<223> OTHER INFORMATION: Trichophyton benhamiae (african) probe

<400> SEQUENCE: 19
cagtgcggct tgacaacac                                           19

<210> SEQ ID NO 20
<211> LENGTH: 20
<212> TYPE: DNA
<213> ORGANISM: Artificial Sequence
<220> FEATURE:
<223> OTHER INFORMATION: Trichophyton concentricum probe

<400> SEQUENCE: 20
aaagttgggg caggggaaga                                          20

<210> SEQ ID NO 21
<211> LENGTH: 25
<212> TYPE: DNA
<213> ORGANISM: Artificial Sequence
<220> FEATURE:
<223> OTHER INFORMATION: Trichophyton erinacei probe
```

-continued

<400> SEQUENCE: 21
ttgcagtgtg ggttagcaac atttg                                          25

<210> SEQ ID NO 22
<211> LENGTH: 220
<212> TYPE: DNA
<213> ORGANISM: Artificial Sequence
<220> FEATURE:
<223> OTHER INFORMATION: Consensus sequence
<220> FEATURE:
<221> NAME/KEY: misc_feature
<222> LOCATION: (4)..(8)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (20)..(23)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(35)
<223> OTHER INFORMATION: n is a, c, g, or t
<220> FEATURE:
<221> NAME/KEY: misc_feature
<222> LOCATION: (38)..(43)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (47)..(49)
<223> OTHER INFORMATION: n is a, c, g, or t
<220> FEATURE:
<221> NAME/KEY: misc_feature
<222> LOCATION: (60)..(61)
<223> OTHER INFORMATION: n is a, c, g, or t
<220> FEATURE:
<221> NAME/KEY: misc_feature
<222> LOCATION: (63)..(64)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (80)..(83)
<223> OTHER INFORMATION: n is a, c, g, or t
<220> FEATURE:
<221> NAME/KEY: misc_feature
<222> LOCATION: (85)..(86)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (95)..(97)

```
<223> OTHER INFORMATION: n is a, c, g, or t
<220> FEATURE:
<221> NAME/KEY: misc_feature
<222> LOCATION: (106)..(107)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (113)..(116)
<223> OTHER INFORMATION: n is a, c, g, or t
<220> FEATURE:
<221> NAME/KEY: misc_feature
<222> LOCATION: (119)..(121)
<223> OTHER INFORMATION: n is a, c, g, or t
<220> FEATURE:
<221> NAME/KEY: misc_feature
<222> LOCATION: (124)..(125)
<223> OTHER INFORMATION: n is a, c, g, or t
<220> FEATURE:
<221> NAME/KEY: misc_feature
<222> LOCATION: (127)..(127)
<223> OTHER INFORMATION: n is a, c, g, or t
<220> FEATURE:
<221> NAME/KEY: misc_feature
<222> LOCATION: (135)..(136)
<223> OTHER INFORMATION: n is a, c, g, or t
<220> FEATURE:
<221> NAME/KEY: misc_feature
<222> LOCATION: (138)..(139)
<223> OTHER INFORMATION: n is a, c, g, or t
<220> FEATURE:
<221> NAME/KEY: misc_feature
<222> LOCATION: (146)..(149)
<223> OTHER INFORMATION: n is a, c, g, or t
<220> FEATURE:
<221> NAME/KEY: misc_feature
<222> LOCATION: (153)..(155)
<223> OTHER INFORMATION: n is a, c, g, or t
<220> FEATURE:
<221> NAME/KEY: misc_feature
<222> LOCATION: (158)..(163)
<223> OTHER INFORMATION: n is a, c, g, or t
<220> FEATURE:
<221> NAME/KEY: misc_feature
<222> LOCATION: (167)..(167)
<223> OTHER INFORMATION: n is a, c, g, or t
<220> FEATURE:
<221> NAME/KEY: misc_feature
<222> LOCATION: (169)..(169)
<223> OTHER INFORMATION: n is a, c, g, or t
<220> FEATURE:
<221> NAME/KEY: misc_feature
<222> LOCATION: (182)..(183)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (189)..(191)
<223> OTHER INFORMATION: n is a, c, g, or t
<220> FEATURE:
<221> NAME/KEY: misc_feature
<222> LOCATION: (193)..(194)
<223> OTHER INFORMATION: n is a, c, g, or t
<220> FEATURE:
<221> NAME/KEY: misc_feature
<222> LOCATION: (200)..(201)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
```

```
<222> LOCATION: (206)..(208)
<223> OTHER INFORMATION: n is a, c, g, or t
<220> FEATURE:
<221> NAME/KEY: misc_feature
<222> LOCATION: (213)..(214)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (219)..(219)
<223> OTHER INFORMATION: n is a, c, g, or t

<400> SEQUENCE: 22
cacnnnnnta accntacccn nnntccnngn ngnnnggnnn nnnancnnnt ggattatggn      60
ntnnttcgtg gantanggtn nnnanncgat cntgnnnatg gcactnntng gtnnnntgnn     120
ncanntncca aaagnngnng cagggnnnna ccnnnttnnn nnntggnang gtgtaggcaa     180
tnnttntgnn ncnncatcgn ngangnnnat cgnngnagna                          220

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
ctggccatgg cacttattgg                                                 20

<210> SEQ ID NO 24
<211> LENGTH: 28
<212> TYPE: DNA
<213> ORGANISM: Artificial Sequence
<220> FEATURE:
<223> OTHER INFORMATION: Probe

<400> SEQUENCE: 24
gatgtaggcc caaaatcatt gcctacac                                        28

<210> SEQ ID NO 25
<211> LENGTH: 22
<212> TYPE: DNA
<213> ORGANISM: Artificial Sequence
<220> FEATURE:
<223> OTHER INFORMATION: Probe

<400> SEQUENCE: 25
ctgccccaac ttttggcaac tg                                              22

<210> SEQ ID NO 26
<211> LENGTH: 21
<212> TYPE: DNA
<213> ORGANISM: Artificial Sequence
<220> FEATURE:
<223> OTHER INFORMATION: Probe

<400> SEQUENCE: 26
taggcaatga ttttgggcct a                                               21

<210> SEQ ID NO 27
<211> LENGTH: 20
<212> TYPE: DNA
<213> ORGANISM: Artificial Sequence
<220> FEATURE:
```

```
<223> OTHER INFORMATION: Probe

<400> SEQUENCE: 27
catcggcgag gaccatcgga                                            20

<210> SEQ ID NO 28
<211> LENGTH: 22
<212> TYPE: DNA
<213> ORGANISM: Artificial Sequence
<220> FEATURE:
<223> OTHER INFORMATION: Probe

<400> SEQUENCE: 28
gcaatggttc tgggcctaca tc                                         22

<210> SEQ ID NO 29
<211> LENGTH: 243
<212> TYPE: DNA
<213> ORGANISM: Artificial Sequence
<220> FEATURE:
<223> OTHER INFORMATION: Sequence from T. rubrum

<400> SEQUENCE: 29
cttttgtgag agagtccagt tgcacgcctg taaccgtacc cgaagtcctt gcagtacggt    60
ttggccacat ttggattatg gagtgcttcg tggactatag tggtgacacg atcctgacca   120
tggcacttat tggtccagtg gggtagttgc caaaagggggc cgcaggggaa gaccgcattc   180
tgaattggaa gagtgtaggc aatggttctg ggcctacatc ggtgatgcat atcggagcag   240
tgc                                                               243

<210> SEQ ID NO 30
<211> LENGTH: 243
<212> TYPE: DNA
<213> ORGANISM: Artificial Sequence
<220> FEATURE:
<223> OTHER INFORMATION: Sequence from T. verrucosum

<400> SEQUENCE: 30
ctattgggag ggagtccagt tgcactcctg taaccgtacc catggtcctt ggcgtgcggg    60
gacataacat ttggattatg ggctccttcg tggattacgg tcccaacacg atcctgacga   120
tggcactcct tgttgacgtg gggcagttgc caaaaggggg ggcaggggaa gaccgaattc   180
atagatggaa gggtgtaggc aatggttctg ggactgcatc ggcgatattt atcggagcag   240
aac                                                               243
```

ASSAY FOR THE DIAGNOSIS OF DERMATOPHYTOSIS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 310159_411_SEQUENCE_LISTING.txt. The text file is 16.8 KB, was created on Jun. 14, 2018, and is being submitted electronically via EFS-Web.

The present invention relates to a primer pair comprising a forward primer and a reverse primer for amplifying a nucleic acid from a pathogen associated with a skin, hair and nail infection comprising SEQ ID NO:22, a nucleic acid capable of hybridizing specifically to a nucleic acid sequence from a pathogen associated with a skin, hair and nail infection comprising SEQ ID NO:22, a carrier comprising the nucleic acid, a method comprising the step detecting in a sample a nucleic acid sequence comprising SEQ ID NO:22 from a pathogen associated with a skin, hair and nail infection, a use of the primer pair, the nucleic acid or the carrier for the diagnosis of a disease and a kit comprising the primer pair, the nucleic acid and/or the carrier for the diagnosis of a disease.

Human pathogenic dermatophytes, which belong to the three genera *Trichophyton, Microsporum* and *Epidermophyton*, are fungi that infect human skin, nails and hair. While the genus *Epidermophyton* is represented only by a single species (*E. floccosum*), the genera *Microsporum* and *Trichophyton* comprised several different species. Recently, several species formerly assigned to *Arthroderma* have been reclassified and assigned to *Trichophyton* (Hoog et al., 2016), and this reassignment will be adhered to throughout this patent application.

Prevalence rates of dermatophyte skin, hair and nail infections in European countries vary between 3 and 22%. Topical therapy is sufficient in most cases, but long term and often expensive systemic treatment is necessary if the infection is caused by specific strains of the genera *Microsporum* and *Trichophyton* such as *T. verrucosum* and *T. mentagrophytes*.

Systemic antifungals are associated with various side effects such as gastro-intestinal side effects, which occur in 3-5% of the patients treated orally with terbinafine. In addition, bone marrow suppression and hepatic side effects may occur albeit less frequent. Therefore, the diagnosis of skin, hair and nail infection with a specific strain should be confirmed before a treatment regime is devised and the therapy initiated.

The current diagnosis of dermatophytes is based on microscopic identification of spores and hyphae in clinical specimens followed by in vitro culture and morphological identification of the fungus. Direct microscopic examination of skin, hair and nail material is often sufficient for the preemptive diagnosis of a fungal infection, but it does not lead to a specific species diagnosis. Although rapid and cheap, this technique has a relatively low sensitivity and shows false negative results in up to 15% of all cases.

Application of culture enables specific species identification in 10-15 days in approximately 95% of cases. However, for some slow growing or atypical isolates time of diagnosis is up to 3-6 weeks. Therefore, a simple rapid and specific method for the diagnosis of dermatophyte infections is required.

PCR-based methods have been introduced for the diagnosis of fungal infections. For example, US2010/0311041 discloses a method for extracting nucleic acids from fungi, a PCR method for detecting fungi in patient samples and a PCR kit for detecting dermatophytes and for diagnosing infections by the three genera *Trichophyton, Microsporum* and *Epidermophyton*.

However, the methods disclosed in the state of the art have shortcomings. In particular, they do not allow the rapid and reliable distinction of closely related strains from the genus *Trichophyton* and *Microsporum*, which includes zoophilic and non-zoophilic species.

Therefore, a problem underlying the present invention is to provide methods and reagents for the diagnosis of a skin, hair and nail disease, preferably a skin, hair and nail infection, more preferably a fungal skin, hair and nail infection.

Another problem underlying the present invention is to provide methods and reagents for identifying and distinguishing from closely related species a pathogen from the genus *Trichophyton*, in particular *T. benhamiae* (yellow) and *T. concentricum*.

The problem underlying the present invention is solved by the subject matter of the attached independent and dependent claims.

In a first aspect, the problem underlying the present invention is solved by a primer pair comprising a forward primer and a reverse primer capable of amplifying a nucleic acid from a pathogen associated with a skin, hair and nail infection comprising SEQ ID NO:22, preferably SEQ ID NO:1.

In a second aspect, the problem underlying the present invention is solved by a nucleic acid capable of hybridizing specifically to a nucleic acid sequence from a pathogen associated with a skin, hair and nail infection comprising SEQ ID NO:22, preferably SEQ ID NO:1, or its complementary strand or a vector or cell comprising said nucleic acid sequence.

In a preferred embodiment, the primer pair or the nucleic acid comprises a detectable label, preferably from the group comprising a fluorescent, radioactive, colloidal gold or enzymatically active label.

In a third aspect, the problem underlying the present invention is solved by a nucleic acid comprising the primer pair according to the present invention and, between the forward and the reverse primer, the nucleic acid sequence from a pathogen associated with a skin, hair and nail infection located in the pathogen's genome between the sequences of the forward and the reverse primer, preferably obtained by amplifying a sample comprising said pathogen using the primers according to the present invention.

In a fourth aspect, the problem underlying the present invention is solved by a carrier comprising the nucleic acid according to the present invention.

In a preferred embodiment, the carrier is a silane coated glass, plastic or silicon material microarray plate.

In a fifth aspect, the problem underlying the present invention is solved by a method comprising the step detecting in a sample a nucleic acid sequence comprising SEQ ID NO:22, preferably SEQ ID NO:1, from a pathogen associated with a skin, hair and nail infection. More preferably the nucleic acid comprises a sequence selected from the group comprising SEQ ID NO:2, SEQ ID NO:3, SEQ ID NO:4, SEQ ID NO:5, SEQ ID NO:6, SEQ ID NO:7, SEQ ID NO:8 and SEQ ID NO:9.

In a preferred embodiment, the method according to the present invention further comprises the steps:

a) providing a sample, preferably nail, hair or skin/nail material, from a patient b) amplifying any nucleic acid comprising SEQ ID NO:22, preferably SEQ ID NO:1, present in the sample using the primer pair, thus generating an amplicon if a nucleic acid sequence comprising SEQ ID NO:22 (or SEQ ID NO:1) from a pathogen associated with a skin, hair and nail infection is present in the sample. More preferably the nucleic acid comprises a sequence selected from the group comprising SEQ ID NO:2, SEQ ID NO:3, SEQ ID NO:4, SEQ ID NO:5, SEQ ID NO:6, SEQ ID NO:7, SEQ ID NO:8 and SEQ ID NO:9 and a variant thereof.

In a preferred embodiment, the method according to the present invention further comprises the step:

c) detecting the amplicon.

In a preferred embodiment, the amplicon is detected by fluorescence, radioactivity, colloidal gold or chemiluminescence.

In a sixth aspect, the problem underlying the present invention is solved by a use of the primer pair, the nucleic acid or the carrier according to the present invention for the diagnosis of a disease, preferably a skin, hair and nail infection associated with a pathogen.

In a seventh aspect, the problem underlying the present invention is solved by a kit comprising the primer pair, the nucleic acid and/or the carrier according to the present invention, preferably for the diagnosis of a disease, more preferably a skin, hair and nail infection associated with a pathogen.

In an eighth aspect, the problem underlying the present invention is solved by a use of the primer pair, the nucleic acid or the carrier according to the present invention for the manufacture of a kit for the diagnosis of a disease, preferably a pathogen associated with a skin, hair and nail infection, more preferably with a skin, hair and nail infection having a nucleic acid comprising SEQ ID NO:22, preferably SEQ ID NO:1.

In an ninth aspect, the problem underlying the present invention is solved by a use of the primer pair, nucleic acid, carrier, use or kit for the identification of a fungus, preferably from the genus *Trichophyton*, more preferably from the group comprising *T. tonsurans, T. equinum, T. interdigitale, T. benhamiae* (african), *T. benhamiae* (yellow), *T. concentricum, T. erinacei* (african) and *T. erinacei*.

In a preferred embodiment, the pathogen is from the group comprising *Trichophyton*.

In a preferred embodiment, the pathogen is from the group comprising *T. tonsurans, T. equinum, T. interdigitale, T. benhamiae* (african), *T. benhamiae* (yellow), *T. concentricum, T. erinacei* (african) and *T. erinacei*.

The present invention is based on the inventors' surprising finding that various pathogens associated with a skin, hair and nail infection have in common a homologous metalloprotease related to the consensus sequence SEQ ID NO:22 or SEQ ID NO:1, with slight, but distinctive sequence differences between relevant strains, which differences may be used to distinguish in samples such as clinical samples from patients suffering from a skin, hair and nail infection various closely related strains of pathogens associated with a skin, hair and nail infection, preferably from the genus *Trichophyton*, and more preferably from the group comprising *T. tonsurans, T. equinum, T. interdigitale, T. benhamiae* (white), *T. benhamiae* (african), *T. benhamiae* (yellow), *T. concentricum, T. erinacei* (african) and *T. erinacei*.

In preferred embodiments of the primer pair comprising a forward primer and a reverse primer capable of amplifying a nucleic acid from a pathogen associated with a skin, hair and nail infection, the pathogen is selected from the group comprising *T. tonsurans, T. equinum, T. interdigitale, T. benhamiae* (white), *T. benhamiae* (african), *T. benhamiae* (yellow), *T. concentricum, T. erinacei* (african) and *T. erinacei*.

In preferred embodiments of the nucleic acid capable of hybridizing specifically to a nucleic acid sequence from a pathogen associated with a skin, hair and nail infection, the pathogen is selected from the group comprising *T. tonsurans, T. equinum, T. interdigitale, T. benhamiae* (african), *T. benhamiae* (yellow), *T. concentricum, T. erinacei* (african) and *T. erinacei*.

According to the present invention, a nucleic acid comprising SEQ ID NO:22 or 1 from a pathogen associated with a skin, hair and nail infection is detected. In a preferred embodiment, the SEQ ID NO:22 or 1 is from a pathogen from the genus *Trichophyton*, more preferably from a pathogen from the group comprising *T. tonsurans, T. equinum, T. interdigitale, T. benhamiae* (white), *T. benhamiae* (african), *T. benhamiae* (yellow), *T. concentricum, T. erinacei* (african) and *T. erinacei*. In a preferred embodiment, the SEQ ID NO:22 or 1 is from *T. tonsurans* and is represented by SEQ ID NO:2. In another preferred embodiment, the SEQ ID NO:22 or 1 is from *T. equinum* and is represented by SEQ ID NO:3. In another preferred embodiment, the SEQ ID NO:22 or 1 is from *T. interdigitale* (anthrophilic+zoophilic), I, II, II, III*, IV, M and is represented by SEQ ID NO:4. In another preferred embodiment, the SEQ ID NO:22 or 1 is from *T. benhamiae* (yellow) and is represented by SEQ ID NO:5. In another preferred embodiment, the SEQ ID NO:22 or 1 is from *T. benhamiae* (white) and is represented by SEQ ID NO:6. In another preferred embodiment, the SEQ ID NO:22 or 1 is from *T. benhamiae* (african) and is represented by SEQ ID NO:7. In another preferred embodiment, the SEQ ID NO:22 or 1 is from *T. concentricum* and is represented by SEQ ID NO:8. In another preferred embodiment, the SEQ ID NO:22 or 1 is from *T. erinacei* and is represented by SEQ ID NO:9.

The invention contemplates various reagents such as a primer pair comprising a forward primer and a reverse primer for amplifying a nucleic acid encoding said metalloprotease from a pathogen. Methods how to design a primer such that specific hybridization is ensured and primer dimerization or secondary structure formation is avoided are described in the state of the art, for example in Dennis, Y. M., Chius, R. W. K., and Allen Chan, K. C. (2006) Clinical applications of PCR, Humana Press, page 18. In a preferred embodiment, each primer has a length of 10 to 40, more preferably 12 to 35, more preferably 14 to 30 nucleotides. In a preferred embodiment, the term "forward primer", as used herein, relates to a primer hybridizing upstream of SEQ ID NO:22 or 1 in the pathogen's genome such that the primer may be extended in a PCR reaction in the 5' to 3' direction, resulting in the synthesis of a nucleic acid comprising SEQ ID NO:22 or 1.

In a preferred embodiment, the forward primer is a universal forward primer hybridizing specifically to a region of the pathogen's genome upstream of SEQ ID NO22 or 1 that is sufficiently conserved among the pathogens to be distinguished, preferably species from the genus *Trichophyton*, to the effect that it may be used to amplify SEQ ID NO22 or 1 of more than one species, even though variable parts of SEQ ID NO22 or 1 of said species differ. In a preferred embodiment, the forward primer hybridizes to a conserved region shared by *T. tonsurans, T. equinum* and *T. interdigitale* (anthrophilic+zoophilic), I, II, III, III*, IV, M, and comprises a sequence comprising GGGAGGGA-GACTAGTTG (SEQ ID NO: 10) or a variant thereof. In another preferred embodiment, the forward primer binds to a conserved region shared by *T. benhamiae* (yellow), *T. benhamiae* (white), *T. benhamiae* (african) *T. concentricum* and *T. erinacei*, and comprises a sequence comprising GCATTTCCCATGGCT (SEQ ID NO: 11) or a variant thereof.

In a preferred embodiment, the term "reverse primer", as used herein, relates to a primer hybridizing specifically downstream of SEQ ID NO:22 or 1 in the pathogen's genome such that the primer may be extended in a PCR reaction in the 5' to 3' direction, resulting in the synthesis of a nucleic acid comprising a sequence complementary to SEQ ID NO:22 or 1.

In a preferred embodiment, the reverse primer is a universal reverse primer hybridizing specifically to a region of the pathogen's genome downstream of SEQ ID NO22 or 1 that is sufficiently conserved among the pathogens to be distinguished, preferably species from the genus *Trichophyton*, to the effect that it may be used to amplify the sequences complementary to SEQ ID NO22 or 1 of more than one species, even though the sequences comprising SEQ ID NO22 or 1 and the sequences complementary to them of said species differ. In a preferred embodiment, the reverse primer hybridizes to a conserved region shared by *T. tonsurans, T. equinum* and *T. interdigitale* (anthrophilic+zoophilic), I, II, III, III*, IV, M, and comprises a sequence comprising AATTTTTCGCCGCCAAG (SEQ ID NO: 12) or a variant thereof. In another preferred embodiment, the reverse primer binds to a conserved region shared by *T. benhamiae* (yellow), *T. benhamiae* (white), *T. benhamiae* (african), *T. concentricum* and *T. erinacei*, and comprises a sequence comprising TGGCTCTGTTACGTG (SEQ ID NO: 13) or a variant thereof.

In another preferred embodiment, the primer pair may be present in a composition comprising more than one primer pair, for example 2, 3, 4, 5, 6, 7, 8, 9, 10, 11, 12, 13, 14, 15, 16, 17, 18, 19, 20, 24, 28, 32, 36, 40 or 48 or more primer pairs. In a preferred embodiment, the composition comprises a primer pair that may be used for amplifying the nucleic acids encoding SEQ ID NO:22 or 1 from *T. tonsurans, T. equinum* and *T. interdigitale* (anthrophilic+zoophilic), I, II, III, III*, IV, M and in addition a primer pair that may be used for amplifying the nucleic acids encoding SEQ ID NO:22 or 1 from *T. benhamiae* (yellow), *T. benhamiae* (white), *T. benhamiae* (african), *T. concentricum* and *T. erinacei*. In a preferred embodiment, the composition may comprise a primer pair that may be used to amplify or detect, by specifically hybridizing to it, one or more sequences that may be used to distinguish pathogens associated with a skin, hair and nail infection, preferably a sequence selected from the group comprising the nucleic acid sequences referred to as beta tubulin (Rezaei-Matehkolaei et al. (2014) Nucleotide sequence analysis of beta tubulin gene in a wide range of dermatophytes, Medical Mycology 42, 674), transcription elongation factor (Mirhendi et al. (2015), Translation elongation factor 1-alpha gene as a potential taxonomic and identification marker in dermatophytes, Medical Mycology 53, 215), internal transcribed spacer regions 1 and 2 (Gräser et al. (2008), The New Species Concept in Dermatophytes—a Polyphasic Approach, Mycopathologia 166, 239) and topoisomerase or a part thereof. Such primer composition may be used according to the present invention and analysed using a carrier comprising one or more nucleic acids capable of hybridizing specifically to a sequence selected from the group comprising the nucleic acid sequences referred to as beta tubulin, transcription elongation factor, internal transcribed spacer regions 1 and 2, and topoisomerase or a part thereof may be used to detect the presence of any such sequence.

The distance between the final base pair of the forward primer, in its 5'-3' orientation, and the first base pair of SEQ ID NO:22 or 1, in its 5'-3' orientation, is, in order of increasing preference, 10 000, 8 000, 6 000, 4 000, 2 000, 1 000, 800, 600, 400, 200, 100 or less base pairs.

The distance between the final base pair of the reverse primer, in its 5'-3' orientation, and the final base pair of SEQ ID NO:22 or 1, in its 5'-3' orientation, is, in order of increasing preference, 10 000, 8 000, 6 000, 4 000, 2 000, 1 000, 800, 600, 400, 200, 100 or less base pairs.

The teachings of the present invention may not only be carried out using nucleic acids having the exact sequences referred to in this application explicitly, for example by function, name, sequence or accession number, or implicitly, but also using variants of such nucleic acids. In a preferred embodiment, the term "variant" of a nucleic acid comprises nucleic acids having at least 70, more preferably 75, 80, 85, 90, 95, 98, 99 or 99.5% sequence identity with the reference or wild type nucleic acid, preferably with the ability to hybridize specifically to the same target as reference or wild type nucleic acid, as well as nucleic acids the complementary strand of which hybridizes, preferably under stringent conditions, to the reference or wild type nucleic acid. In a preferred embodiment, the term "hybridizes specifically", as used herein, means that a nucleic acid such as a primer or probe hybridizes under stringent conditions to the target nucleic acid. Stringency of hybridization reactions is readily determinable by one of ordinary skilled in the art, and in general is an empirical calculation dependent on primer or probe length, reaction temperature and salt concentration. In general longer primers or probes withstand higher temperatures for proper annealing, while shorter primers or probes less so. Hybridization generally depends on the ability of single or double stranded DNA to bind to complementary strands present in an environment below their melting temperature. The higher the degree of desired homology between the probe and hybridizable sequence, the higher the relative temperature which may be used. As a result higher relative temperatures would tend to make the reaction conditions more stringent and beware unspecific bindings, while lower temperature less so. For additional details and explanation of stringency of hybridization reactions, see Ausubel, F. M. (1995), Current Protocols in Molecular Biology. John Wiley & Sons, Inc. Moreover, the person skilled in the art may follow the instructions given in the manual Boehringer Mannheim GmbH (1993) The DIG System Users Guide for Filter Hybridization, Boehringer Mannheim GmbH, Mannheim, Germany and in Liebl, W., Ehrmann, M., Ludwig, W., and Schleifer, K. H. (1991) International Journal of Systematic Bacteriology 41: 255-260 on how to identify DNA sequences by means of hybridization. In a preferred embodiment, stringent conditions are applied for any hybridization, i.e. hybridization occurs only if the primers or probe is 70%, preferably 75%, 80%, 85%, 90%, 95% or 99% or more identical to the target sequence. Nucleic acid having a lower degree of identity with respect to the target sequence may hybridize, but such hybrids are unstable and will be removed while the annealing step of a PCR or the washing steps after probe hybridization. In a washing step of a probe hybridization under stringent conditions, for example lowering the concentration of salt to 2×SSC or, optionally and subsequently, to 0.25×SSC, while the temperature is, in order of increasing preference, approximately 39° C.-69° C., approximately 41° C.-67° C., approximately 43° C.-65° C., approximately 45° C.-63° C., approximately 47° C.-61° C., approximately 49° C.-59° C., approximately 51° C.-57° C., approximately 53° C.-57° C. In a particularly preferred embodiment, the temperature is approximately 51° C.-57° C. or approximately 53° C.-57° C. In a preferred embodiment, the primer pair used in a PCR reaction comprises a detectable label, preferably from the group comprising a fluorescent, radioactive, colloidal gold or enzymatically active label. More preferably, the label is a fluorescent label preferably selected from the group comprising cy-3, cy-5, HEX, FAM, ROX and TAMRA. Suitable labels, ways to link them to nucleic acids such as primers and to detect such labels have been described in the state of the art.

In a preferred embodiment, the nucleotide sequence of each primer of the primer pair and/or the probe of the invention comprises or consists of a sequence that is capable of amplifying or hybridizing to a sequence set forth in SEQ ID NO:22, 1 or the complement sequence thereof with the proviso that said primer pair and/or said probe is not capable to amply or hybridize to a sequence set forth in SEQ ID NO:6, 29, 30 and/or the complement sequence thereof. Thus, in some embodiments the probe of the invention comprises or consists of a sequence that is capable of hybridizing to a sequence set forth in SEQ ID NO:22 or the complement sequence thereof with the proviso that said probe is not capable to hybridize to a sequence set forth in SEQ ID NO:6, 29, 30 and/or the complement sequence thereof. In alternative embodiments, the probe of the invention comprises or consists of a sequence that is capable of hybridizing to a sequence set forth in SEQ ID NO:1 or the complement sequence thereof with the proviso that said probe is not capable to hybridize to a sequence set forth in SEQ ID NO:6, 29, 30 and/or the complement sequence thereof. Stringent conditions for hybridization are described above. Methods for the measurement of nucleotide hybridization are well-known in the art. In embodiments concerning the proviso that the primer pair and/or the probe of the invention is not capable to amply or hybridize to a sequence set forth in SEQ ID NO:6, 29, 30 and/or the complement sequence thereof, said sequence has a sequence identity of at least 85%, at least 90%, at least 95%, at least 96%, at least 97, at least 98%, at least 99% or 100% to a sequence set forth in SEQ ID NO:6, 29, 30 and/or the complement sequence thereof over its entire length.

In preferred embodiments, the nucleotide sequence of each primer of the primer pair and/or the probe of the invention comprises or consists of a sequence that is capable of amplifying or hybridizing to a sequence set forth in SEQ ID NO:22, 1 or the complement sequence thereof, wherein said nucleotide sequence of each primer of the primer pair and/or the probe of the invention comprises or consists of a sequence that is a fragment of the sequence set forth in SEQ ID NO:22, 1 or the complement sequence thereof, wherein said fragment has at least 80%, at least 85%, at least 90%, at least 95%, at least 96%, at least 97, at least 98%, at least 99% or 100% sequence identity to a sequence set forth in SEQ ID NO:22, 1 or the complement sequence thereof over a length of at least 5, at least 10, at least 15, at least 16, at least 17, at least 18, at least 19, at least 20, at least 21, at least 22, at least 23, at least 24, at least 25 or at least 26 consecutive nucleotides. Thus, in some embodiments the nucleotide sequence of the probe of the invention comprises or consists of a sequence that is a fragment of the sequence set forth in SEQ ID NO:22 or the complement sequence thereof, wherein said fragment has at least 90% sequence identity to the sequence set forth in SEQ ID NO:22 or the complement sequence thereof over a length of at least 5, at least 10, at least 15, at least 16, at least 17, at least 18, at least 19, at least 20, at least 21, at least 22, at least 23, at least 24, at least 25 or at least 26 consecutive nucleotides. In some embodiments the nucleotide sequence of the probe of the invention comprises or consists of a sequence that is a fragment of the sequence set forth in SEQ ID NO:22 or the complement sequence thereof, wherein said fragment has at least 95% sequence identity to the sequence set forth in SEQ ID NO:22 or the complement sequence thereof over a length of at least 5, at least 10, at least 15, at least 16, at least 17, at least 18, at least 19, at least 20, at least 21, at least 22, at least 23, at least 24, at least 25 or at least 26 consecutive nucleotides. in some embodiments the nucleotide sequence of the probe of the invention comprises or consists of a sequence that is a fragment of the sequence set forth in SEQ ID NO:22 or the complement sequence thereof, wherein said fragment has at least 98% sequence identity to the sequence set forth in SEQ ID NO:22 or the complement sequence thereof over a length of at least 5, at least 10, at least 15, at least 16, at least 17, at least 18, at least 19, at least 20, at least 21, at least 22, at least 23, at least 24, at least 25 or at least 26 consecutive nucleotides. in some embodiments the nucleotide sequence of the probe of the invention comprises or consists of a sequence that is a fragment of the sequence set forth in SEQ ID NO:22 or the complement sequence thereof, wherein said fragment has 100% sequence identity to the sequence set forth in SEQ ID NO:22 or the complement sequence thereof over a length of at least 5, at least 10, at least 15, at least 16, at least 17, at least 18, at least 19, at least 20, at least 21, at least 22, at least 23, at least 24, at least 25 or at least 26 consecutive nucleotides.

In preferred embodiments, the probe of the invention has a length of not more than 250, not more than 200, not more than 150, not more than 100, not more than 90, not more than 80, not more than 70, not more than 65, not more than 60, not more than 55, not more than 50, not more than 45, not more than 40, not more than 35, not more than 30, not more than 25 or not more than 20 nucleotides fused to a detectable signal molecule.

In some embodiments the nucleotide sequence of the probe of the invention comprises or consists of a sequence that is a fragment of the sequence set forth in SEQ ID NO:1 or the complement sequence thereof, wherein said fragment has at least 90% sequence identity to the sequence set forth in SEQ ID NO:1 or the complement sequence thereof over a length of at least 5, at least 10, at least 15, at least 16, at least 17, at least 18, at least 19, at least 20, at least 21, at least 22, at least 23, at least 24, at least 25 or at least 26 consecutive nucleotides. In some embodiments the nucleotide sequence of the probe of the invention comprises or consists of a sequence that is a fragment of the sequence set forth in SEQ ID NO:1 or the complement sequence thereof, wherein said fragment has at least 95% sequence identity to the sequence set forth in SEQ ID NO:1 or the complement sequence thereof over a length of at least 5, at least 10, at least 15, at least 16, at least 17, at least 18, at least 19, at least 20, at least 21, at least 22, at least 23, at least 24, at least 25 or at least 26 consecutive nucleotides. in some embodiments the nucleotide sequence of the probe of the invention comprises or consists of a sequence that is a fragment of the sequence set forth in SEQ ID NO:1 or the complement sequence thereof, wherein said fragment has at least 98% sequence identity to the sequence set forth in SEQ ID NO:1 or the complement sequence thereof over a length of at least 5, at least 10, at least 15, at least 16, at least 17, at least 18, at least 19, at least 20, at least 21, at least 22, at least 23, at least 24, at least 25 or at least 26 consecutive nucleotides. in some embodiments the nucleotide sequence of the probe of the invention comprises or consists of a sequence that is a fragment of the sequence set forth in SEQ ID NO:1 or the complement sequence thereof, wherein said fragment has 100% sequence identity to the sequence set forth in SEQ ID NO:1 or the complement sequence thereof over a length of at least 5, at least 10, at least 15, at least 16, at least 17, at least 18, at least 19, at least 20, at least 21, at least 22, at least 23, at least 24, at least 25 or at least 26 consecutive nucleotides.

In other preferred embodiments of the invention, the above described properties of each primer of the primer pair and the probe of the invention are combined, namely (1) that said primer pair and/or said probe is not capable to amply or hybridize to a sequence set forth in SEQ ID NO:6, 29, 30 and/or the complement sequence thereof, (2) that the probe of the invention has a limited length and (3) that each primer of the primer pair and the probe of the invention comprise a fragment of SEQ ID NO:22 or the complement sequence thereof, wherein said fragment has at least 90% sequence identity to the sequence set forth in SEQ ID NO:22 or the complement sequence thereof over a length of at least 5 consecutive nucleotides.

According to the present invention, a nucleic acid capable of hybridizing specifically to a nucleic acid sequence comprising SEQ ID NO:22 or 1 from a pathogen associated with a skin, hair and nail infection or its complementary strand is provided. The nucleic acid may be an isolated nucleic acid. This nucleic acid may be used as a probe to detect the nucleic acid comprising SEQ ID NO:22 or 1 from the pathogen and to distinguish it from other sequences, more specifically homologous sequences from other pathogens associated with such an infection also comprising SEQ ID NO:22 or 1. Therefore, this nucleic acid comprises a strand capable of hybridizing specifically to the sequence comprising SEQ ID NO:22 or 1 or a complementary sequence. Preferably the nucleic acid capable of hybridizing specifically to a nucleic acid sequence comprising SEQ ID NO:22 or 1 from such a pathogen is selected from the group comprising SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:s. 24 to 28 and a variant thereof.

The nucleic acid capable of hybridizing specifically to a nucleic acid sequence from a pathogen associated with a skin, hair and nail infection comprising SEQ ID NO:22 or 1 may be immobilized, preferably on a carrier. This way, it is more straightforward to separate said nucleic acid when it is annealed to a nucleic acid from a pathogen comprising SEQ ID NO:22 or 1 from any other nucleic acids or other substances in a sample from a patient. The carrier may be made by coating a carrier with a nucleic acid capable of hybridizing specifically to a nucleic acid comprising SEQ ID NO:22 or 1 or a variant thereof, more preferably a nucleic acid comprising a sequence selected from the group comprising SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:s. 24 to 28 and a variant thereof. In a preferred embodiment, the carrier is a microarray plate. Suitable microarrays, ways how to prepare and how to use them are described in the state of the art, for example in Müller, H. J & Röder, T. (2004) Der Experimentator—Microarrays, Elsevier/Spektrum, Chapters 3 and 4.

According to the present invention, a method comprising the step detecting in a sample a nucleic acid comprising SEQ ID NO:22 or 1 from a pathogen associated with a skin, hair and nail infection is provided. In a preferred embodiment, the term "detecting", as used herein, means that the presence or absence of SEQ ID NO:22 or 1 or a variant thereof is detected. In a more preferred embodiment, the term means that it is determined whether or not the nucleic acid present comprises SEQ ID NO:22 or 1 from one or more pathogens from the genus *Trichophyton*, and more preferably from the group comprising *T. tonsurans, T. equinum, T. interdigitale, T. benhamiae* (white), *T. benhamiae* (african), *T. benhamiae* (yellow), *T. concentricum, T. erinacei* (african), *T. erinacei* and *T. concentricum* and optionally which of these pathogens' sequence it is. In a most preferred embodiment, the term means that it is determined whether or not a nucleic acid present in the sample is from *T. benhamiae* (yellow) or *T. concentricum*, thus distinguishing both organisms. In another preferred embodiment, the detection may be a semi-quantitative or quantitive detection. Methods that may be used to detect a specific sequence are described in the state of the art, for example in Lottspeich, F. & Engels, J. W. (2012), Bioanalytik, Springer Spektrum, $3^{rd}$ edition. In a preferred embodiment, the method is selected from the group comprising microarray, nucleic acid sequencing, mass spectrometry and PCR, more preferably real-time PCR. In another preferred embodiment, the pathogen associated with a skin, hair and nail infection is detected by identifying the polypeptide partially encoded by SEQ ID NO:22 or 1. The person skilled in the art is familiar with suitable methods, preferably selected from the group comprising immunoassays and mass spectrometry. Antibodies may be generated for distinguishing differences between nucleic acid sequences comprising SEQ ID NO:22 or 1 at the protein level using standard methods described in the state of the art, for example Lottspeich, F. & Engels, J. W. (2012), Bioanalytik, Chapter 6.

The method according to the present invention may optionally comprise detecting in a sample one or more additional nucleic acid sequences in addition to the nucleic acid from a pathogen associated with a skin, hair and nail infection. Such a sequence may be another SEQ ID NO:22 or 1 from a pathogen associated with a skin, hair and nail infection. For example, the method may involve detecting a first nucleic acid comprising SEQ ID NO:22 or 1 from a pathogen from the group *T. tonsurans, T. equinum* and *T. interdigitale* (anthrophilic+zoophilic), I, II, III, III*, IV, M, and a second nucleic acid comprising another SEQ ID NO:22 or 1 from a pathogen from the group comprising *T. benhamiae* (yellow), *T. benhamiae* (white), *T. benhamiae* (african), *T. concentricum* and *T. erinacei*. Such additional sequences are preferably detected simultaneously together with the sequence encoding a metalloprotease from a pathogen associated with a skin, hair and nail disease. In a preferred embodiment, a multiplex PCR reaction is carried out to amplify the sequences to be detected, and this may optionally be followed by microarray analysis, preferably using fluorescence detection of the amplicons comprising SEQ ID NO:22 or 1 of the sequence encoding a metalloprotease and any amplicons comprising one of the additional sequences.

In a preferred embodiment, the method may comprise step a) providing a sample, preferably from a patient. A sample examined using a method or reagent according to the present invention may be obtained from a patient suspected of suffering from a skin, hair and nail infection and is preferably a sample from a part of the patient's body which comprises keratin. In a more preferred embodiment, the sample is a nail, hair or skin sample, more preferably an isolated sample. The patient is preferably a mammalian patient, more preferably a human. Alternatively, the sample may be an environmental sample, for example from soil or the floor of potentially contaminated areas such as a swimming pool or a hospital. Prior to further analysis, the sample may be processed, for example by extracting any nucleic acids present. In a preferred embodiment, the term "extracting", as used herein, means that the nucleic acids are purified from the sample and/or concentrated, for example to remove any contaminants that may interfere with the amplification and/or detection. In a preferred embodiment, the nucleic acid is DNA or RNA, more preferably DNA. Methods and reagents for extracting nucleic acids, preferably for detecting pathogens, more preferably fungal pathogens, are commercially available. It is possible to use the sample directly or the extracted nucleic acid for the detection, but it is preferred that the method comprises step b) amplifying any nucleic acid comprising SEQ ID NO:22 or 1 and optionally any additional sequence or sequences, thus generating one or more amplicons. Such amplification may be performed by PCR. Suitable methods and reagents are described in the state of the art, for example in Dennis, Y. M., Chius, R. W. K., and Allen Chan, K. C. (2006) Clinical applications of PCR, Humana Press, chapter 1. Essentially the sample or the nucleic acid extracted is contacted with at least one primer pair according to the present invention and optionally additional primer pairs followed by addition of a polymerase capable of amplifying the nucleic acid in the presence of any reagents required such as NTPs and bivalent cations in a PCR buffer. The resulting reaction mixture is subjected to several amplification cycles each comprising a denaturation step, which involves separating the two complementary strands of the nucleic acid, an annealing step, which sees the primers hybridize to the nucleic acid strands and an elongation reaction which involves the generation of complementary strands to both strands of the nucleic acid. As a result, a double-stranded amplicon is generated that comprises the primer pair and the sequence from the genomic nucleic acid of the pathogen located between the forward and the reverse primers of the primer pair. The amplicon is present at a concentration that exceeds the concentration of the nucleic acid in the sample, preferably, in order of increasing preference, more than 10, $10^2$, $10^3$, $10^4$ or $10^5$ times. Several reactions for the PCR amplification and generation of amplicons comprising additional sequences may be carried out. The forward and/or reverse primers may be labeled, resulting in a labeled amplicon.

In a preferred embodiment, the primer pair used in a PCR reaction comprises a detectable label, preferably from the group comprising a fluorescent, radioactive, colloidal gold or enzymatically active label. More preferably, the label is a fluorescent label preferably selected from the group comprising cy-3, cy-5, HEX, FAM, ROX and TAMRA. Suitable labels, ways to link them to nucleic acids such as primers and to detect such labels have been described in the state of the art.

Subsequently or concomitantly as step b) is carried out, any amplicon may be labeled, preferably by fluorescence, radioactivity, colloidal gold or chemiluminescence. In a preferred embodiment, the label may be linked to the primers prior to carrying out step b), for example if a fluorescent, radioactive, enzymatically active or chemiluminescent label is attached to one or both primers of the primer pair. In another preferred embodiment, the amplicon may be labeled as the amplification reaction progresses, for example by incorporation of labeled NTPs or a parallel labeling reaction. In another preferred embodiment, the amplicon may be labeled following step b), for example by attaching to the amplicon a fluorescent, radioactive, enzymatically active or chemiluminescent label or by adding to the amplicon a label binding to double-stranded DNA, for example a fluorescent intercalating agent such as ethidium or propidium bromide.

Subsequently or concomitantly as step b) is carried out, the amplicon or amplicons may be detected. For example, the PCR may be real-time PCR involving continuous fluorescence detection as the reaction progresses. If the amplicon is to be detected subsequently, the amplicon may be extracted from the PCR reaction mixture prior to step c). For a subsequent detection, the amplicon, extracted or not, may be contacted, under conditions allowing for a specific hybridization, with a nucleic acid capable of specifically hybridizing to a nucleic acid from a pathogen comprising SEQ ID NO:22 or 1, preferably a nucleic acid comprising a sequence from the group comprising SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:s. 24 to 28 and a variant thereof. The nucleic acid comprising SEQ ID NO:22 or 1 is preferably immobilized on a carrier. It may be subjected to a washing step to remove contaminants prior to carrying out the detection. In such a setting, it is preferred that the amplicon is labeled and the label is detected in case a labeled amplicon present hybridized specifically to the nucleic acid comprising SEQ ID NO:22 or 1.

Preferably, the detection is carried out such that an amplicon comprising SEQ ID NO:22 or 1 from a pathogen associated with a skin, hair and nail disease may be distinguished from an amplicon comprising SEQ ID NO:22 or 1 from another pathogen associated with a skin, hair and nail disease or an amplicon comprising an additional or in fact any other sequence.

According to the present invention, a kit comprising the primer pair, the nucleic acid and/or the carrier may be provided. The primer pair or the nucleic acid may be labeled. The inventive teachings provide a kit, preferably for diagnosing a disease. The kit may comprise instructions detailing how to use the kit and a means for contacting the nucleic acid capable of hybridizing specifically to SEQ ID NO:22 or 1 from a pathogen with a sample from a subject, preferably a human subject, on a carrier, for example, a microarray. Furthermore, the kit may comprise a positive control, for example one or more nucleic acids comprising SEQ ID NO:22 or 1 from a pathogen associated with a skin, hair and nail disease, and a negative control, for example a nucleic acid lacking SEQ ID NO:22 or 1. Finally, such a kit may comprise a standard solution comprising one or more nucleic acids comprising SEQ ID NO:22 or 1 from a pathogen associated with a skin, hair and nail disease for preparing a calibration curve. In a preferred embodiment, the SEQ ID NO:22 or 1 is from a pathogen from the genera *Microsporum* and *Trichophyton*, more preferably from a pathogen from the group comprising *T. tonsurans, T. equinum, T. interdigitale, T. benhamiae* (white), *T. benhamiae* (african), *T. benhamiae* (yellow), *T. concentricum, T. erinacei* (african) and *T. erinacei*.

According to the present invention, the primer pair, carrier, nucleic acid, cell, vector or kit may be used for the diagnosis of a disease or for the manufacture of a kit for the diagnosis of a disease, preferably a skin, hair and nail disease, more preferably a skin, hair and nail infection, more preferably a fungal skin, hair and nail infection, most preferably dermatophytosis. Preferably, said disease is an infection associated with a pathogen from the genus *Trichophyton*, more preferably from a pathogen from the group comprising *T. tonsurans, T. equinum, T. interdigitale, T. benhamiae* (white), *T. benhamiae* (african), *T. benhamiae* (yellow), *T. concentricum T. erinacei* (african) and *T. erinacei*.

In a preferred embodiment, the term "diagnosis", as used herein, refers to any kind of procedure aiming to obtain information supportive in the assessment whether a patient suffers or is likely or more likely than the average or a comparative subject, the latter preferably having similar symptoms, to suffer from a certain disease or disorder in the past, at the time of the diagnosis or in the future, to find out how the disease is progressing or is likely to progress in the future or to evaluate the responsiveness of a patient with regard to a certain treatment, for example the administration of suitable drugs such as drugs for the desensitization of allergic patients. In other words, the term "diagnosis" comprises not only diagnosing, but also prognosticating and/or monitoring the course of a disease or disorder.

Therefore, the term "diagnosis" does preferably not imply that the diagnostic methods or agents according to the present invention will be definitive and sufficient to finalize the diagnosis on the basis of a single test, let alone parameter, but may refer to a contribution to what is referred to as a "differential diagnosis", i.e. a systematic diagnostic procedure considering the likelihood of a range of possible conditions on the basis of a range of diagnostic parameters. This may include an indirect diagnosis, i.e. a negative result means that one disease may be ruled out but that, in turn, another disease is more likely to be present. The term "diagnosis" may also refer to a method or agent used to choose the most promising treatment regime for a patient. In other words, the method or agent may relate to selecting a treatment regimen for a subject. The term "diagnosis" may also refer to the identification of the causative pathogen of a disease or to distinguishing two closely related pathogens, preferably *T. benhamiae* (yellow) or *T. concentricum*.

The present invention is further illustrated by the following non-limiting figures, sequences and examples from which further features, embodiments, aspects and advantages of the present invention may be taken.

BRIEF DESCRIPTION OF THE DRAWINGS

FIG. 1 shows a sequence alignment comprising the various sequences related to a metalloprotease with shared nucleic acid sequence motifs and the consensus sequence derived (SEQ IDS NOS: 4, 2, 6, 9, 7, 3, 5, 8 and 1) respectively.

FIGS. 3A-3D shows captured microarrays with hybridized PCR products from *Trichophyton* benhamiae (yellow) (A), *Trichophyton* benhamiae (white) (B), *Trichophyton* benhamiae (african) (C) and *Trichophyton concentricum* (D) templates. The specific probes for *Trichophyton* benhamiae (yellow) and *Trichopyhton concentricum* are highlighted by a white circle and the dotted encircled spots are controls needed from the software to set the grid. Only the PCR products from the *Trichophyton* benhamiae (yellow) (A) and *Trichophyton concentricum* (D) template hybridized to the specific probes and showed fluorescent signals.

FIGS. 4A-4C shows captured microarrays with hybridized PCR products from *Trichophyton* benhamiae (white) (A), *Trichophyton* benhamiae (yellow) (B) and *Trichophyton* benhamiae (african) (C) templates. The specific probes for *Trichophyton* benhamiae (yellow) and *Trichophyton* benhamiae (white/african) are highlighted by a white circle and the dotted encircled spots are controls needed from the software to set the grid. The PCR products from the *Trichophyton* benhamiae (white) (A), *Trichophyton* benhamiae (yellow) (B) and *Trichophyton* benhamiae (yellow) (C) template hybridized to the specific probes and showed fluorescent signals.

Figure 2B:
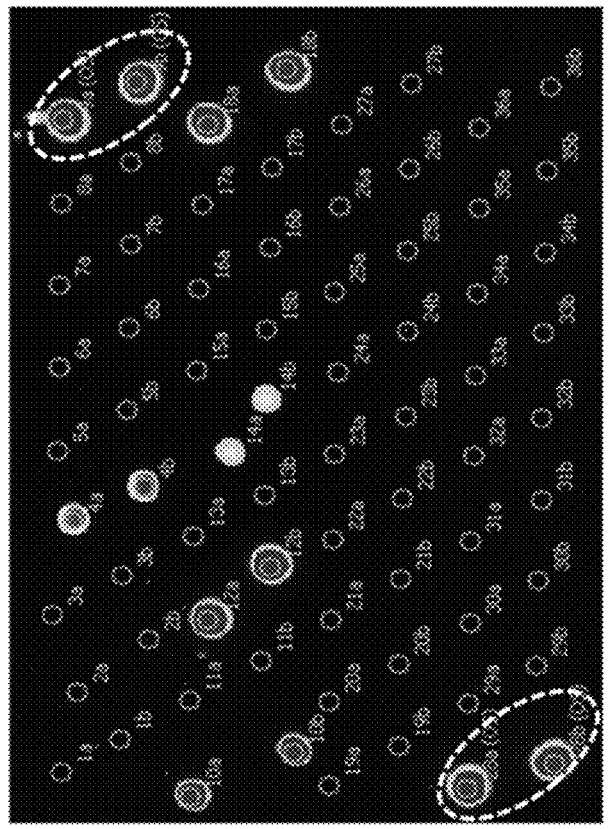
FIGS. 2A-2D shows captured microarrays with hybridized PCR products from *Trichophyton interdigitale* (anthrophilic) (A), *Trichophyton interdigitale* (zoophilic) (B), *Trichophyton tonsurans* (C) and *Trichophyton equinum* (D) templates. The specific probe for *Trichophyton tonsurans* is highlighted by a white circle and the dotted encircled spots are controls needed from the software to set the grid. Only the PCR products from the *Trichophyton tonsurans* template (C) hybridized to the specific probe (6a, 6b) and showed fluorescent signals.
Figure 2A:
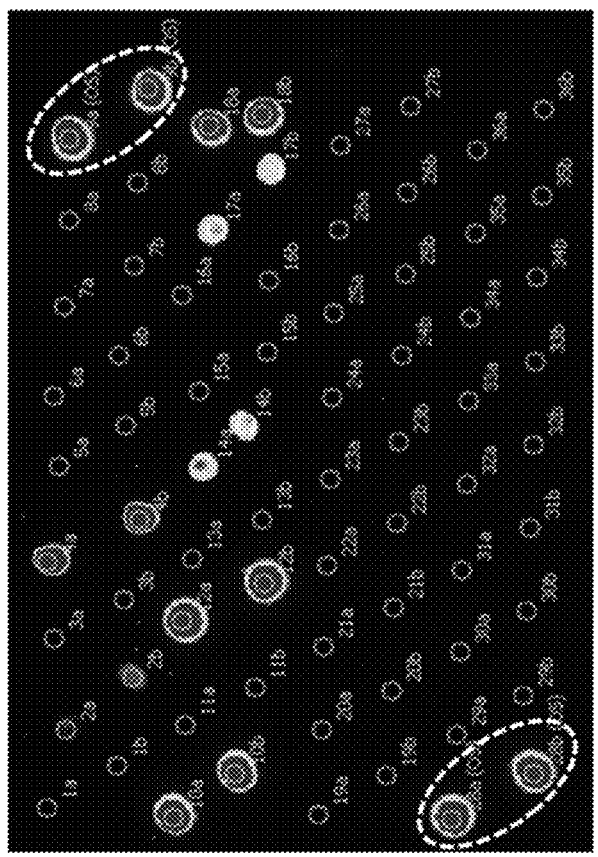
Figure 2D:
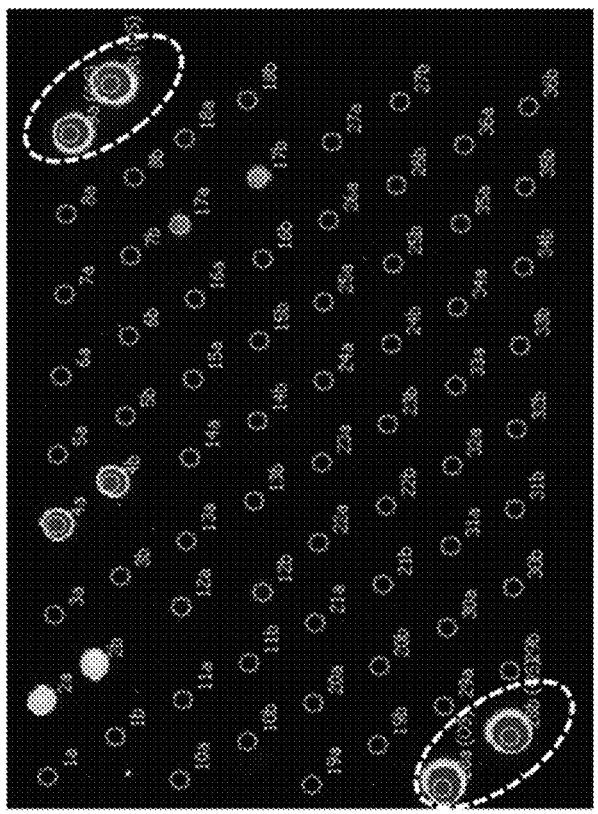
Figure 2C:
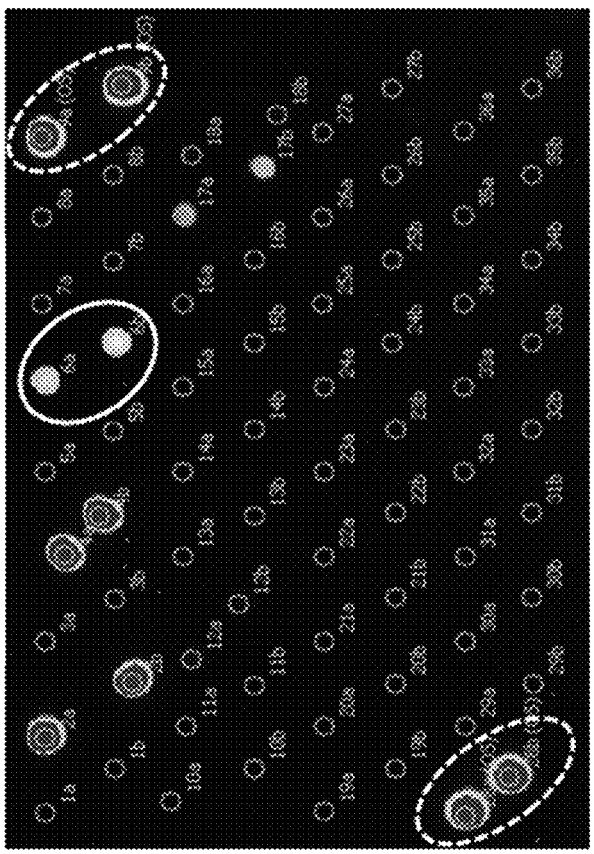

The present invention relates to the following nucleic acid sequences (presented in 5'-3' orientation):

```
SEQ ID NO: 1:
Consensus sequence of metalloprotease-related nucleic acid
to be amplified
CACNNNNNTAACCNTACCCnnnnTCCnnGnnGnnnGGnnnnnnAnCnnnTGGATTATGGnnTnnTT CGTGGAnTAnGGTnnnnAnnCGATCnTGnnnATGGCACTnnTnGGTnnnnTGnGnCAnnTnCCAA AAGnnGnnGCAGGGnnnnnACCnnnTTnnnnnnTGGnAnGGTGTAGGCAATnnTTnTGnGnCnnCA TCGnnGAnGnnnATCGnnGnAGnA
```

-continued

SEQ ID NO: 2:
Target sequence related to metalloprotease from *T. tonsurans*
CACGCTTATAACCGTACCCGA<u>*GATCCTTGGCGTACGGATGCATA*</u>ACGGCTGGATTATGGG

CTCCTTCGTGGATTATGGTCGAGACGCGATCTTGATGATGGCACTTATCGGTGAGATGAGG

CAGTTGCCAAAAGATGTTGCAGGGGAAGACCGAATTCATGGCTGGGAGGGTGTAGGCAAT

AGTTCTGGGACGGCATCGTCGATGTTTATCGTAGCAGAACCACTGAACAGGGCCACCCTC

TGAAACGGATGCTTTGGAAATCGAGTAGAGATGCATGGAAACCTCCTTCCTGGTTGCAGAA

TC

SEQ ID NO: 3:
Target sequence related to metalloprotease from *T. equinum*
CACGCTCATAACCGTACCCG<u>*AGATCCCTGGCGTGCG*</u>GACGCATAACGGCTGGATTATGGG

CTCCTTCGTGGATTATGGTCGAGACGCGATCTTGATGATGGCACTTATCGGTGAGATGAGG

CAGTTGCCAAAAGATGTAGCAGGGGAAGACCGAATTCATGGCTGGGAGGGTGTAGGCAAT

AGTTCTGGGACGGCATCGTCGATGTTTATCGTAGCAGAACCACTGAACAGGGCCACCCTC

TGGAACGGATGCTTTGGAAATCGAGTAGAGATGCATGGAAACCTCCTTCCTGGTTGCAGAA

TC

SEQ ID NO: 4:
Target sequence related to metalloprotease from *T. interdigitale* (anthrophilic + zoophilic), I, II, II, III*, IV, M
CACGGTAATAACCGTACCCGAGGTCCCCGGCGTGCGGACTCATAACGGCTGGATTATGGG

CTCCTTCGTGGATTATGGTCGAGACGCGATCTTGACCATGGCACTTCTTGGTGAGATGGG

GCAGTTGCCAAAAGATGTCGCAGGGAAAGACCGAATTCATGGCTGGGAGGGTGTAGGCAA

TAGTTCTGCGACGGCATCGTCGATGTTTATCGTGGCAGAACCACTTAACAGGGCCACCCTC

TGAAACGGATGCTTTGGAAATCGAGTT<u>*GAGATGCGCGGAAACCTC*</u>CTTCCTGGTTGCAGG

ATC

SEQ ID NO: 5:
Target sequence related to metalloprotease from *T. benhamiae* (yellow)
CTCCGGTGAGAGAGTGCAATTGCACGATCGTAACCGTACCCCAAGTCCTTGCAGAACGGT

GTAACAACCCTTGGATTATGGAGTAATTCGTGGATTATGGTGTCGACACGATCCTGGCCAT

GGCACTTATTGGTTTGGTGGGGCAGTTGCCAAAAGATGGAGCAGGGGAAGACCGAGTTCT

CGCCTGGAAGG<u>*GTGTAGGCAATGATTTTGGGCCTACATC*</u>GGTGACGTGCATCGGAGCAGT

AC

SEQ ID NO: 6:
Target sequence related to metalloprotease from *T. benhamiae* (white)
CTCTGGTGAGAGAGTGCAGTTGCACGATTGTAACCATACCCATGGTCCT<u>*TGCAGTGCGGT*</u>

<u>*GTGACAGCATTTGG*</u>ATTATGGGCTCCTTCGTGGATTACGGTCCCGACACGATCCTGACGAT

GGCACTCATTGGTGCGGTGGGGCAGTTGCCAAAAGAGGGAGCAGGGGTGAACCTCATTC

CTAGCTGGAAAGGTGTAGGCAATGGTTCTGGGACTGCATCGGCGAGGACCATCGGAGCA

GAAC

SEQ ID NO: 7:
Target sequence related to metalloprotease *T. benhamiae* (African)
CTCTTGTGAGAGAGTGCAGTTGCACGCTGATAACCGTACCCATGGTCCTTG<u>*CAGTGCGGC*</u>

<u>*TTGACAACAC*</u>TTGGATTATGGGCTCCTTCGTGGACTACGGTCCCGATACGATCCTGACGAT

-continued

GGCACTTATTGGTGCGGTGGGGCAGTTGCCAAAAGATGTCGCAGGGGTGAACCTCATTCC

TAGATGGAAAGGTGTAGGCAATGGTTCTGGGACCGCATCGGCGAGGACCATCGGAGCAG

AAC

SEQ ID NO: 8:
Target sequence related to metalloprotease from *T. concentricum*
CTCCGGTGAGAGAGTGCAGTTGCACGATTGTAACCGTACCCCAAGTCCTTGCAGAACGGT

GTAACAACACTTGGATTATGGAGTAATTCGTGGATTATGGTGTCGACACGATCCTGGCCAT

GGCACTTATTGGTTTGGTGGGGCAGTTGCCA*AAAGTTGGGGCAGGGGAAGAC*CGAGTTCT

CGCCTGGAAGGGTGTAGGCAATGGTTCTGGGCCTACATCGGTGACGTGCATCGGAGTAGT

AC

SEQ ID NO: 9:
Target sequence related to metalloprotease from *T. erinacei*
CTCCCGTGAGAGAGTGCAGTTGCACTACTGTAACCGTACCCATGGTCC*TTGCAGTGTGGG*

*TTAGCAACATTTG*GATTATGGAGTGCTTCGTGGATTACGGTCCCAACACGATCCTGACCAT

GGCACTTCTTGGTTTTGTGCGCCATATTCCAAAAGATGGGGCAGGGGTGAACCTCATTGTT

AGATGGAAGGGTGTAGGCAATGGTTCTGGGACCGCATCGGCGAGGACCATCGGAGCAGT

A

SEQ ID NO: 10:
Universal forward primer (*Trichophyton tonsurans*, *Trichophyten equinum*, *Trichophyton interdigitale* (antrophilic + zoophilic) I, II, III, III*, IV, M):
GGGAGGGAGACTAGTTG SEQ ID NO: 11:
Universal forward primer (*Trichophyton benhamiae* (yellow), *Trichophyton benhamiae* (white), *Trichophyton benhamiae* (african), *Trichophyton concentricum*, *Trichophyton erinacei*)
GCATTTCCCATGGCT SEQ ID NO: 12:
Universal reverse primer (*Trichophyton tonsurans*, *Trichophyten equinum*, *Trichophyton interdigitale* (antrophilic + zoophilic) I, II, III, III*, IV, M)
AATTTTTCGCCGCCAAG SEQ ID NO: 13:
Universal reverse primer (*Trichophyton benhamiae* (yellow), *Trichophyton benhamiae* (white), *Trichophyton benhamiae* (african), *Trichophyton concentricum*, *Trichophyton erinacei*)
TGGCTCTGTTACGTG SEQ ID NO: 14:
*Trichophyton tonsurans* probe
GATCCTTGGCGTACGGATGCATA SEQ ID NO: 15:
*Trichophyten equinum* probe
AGATCCCTGGCGTGCG SEQ ID NO: 16:
*Trichophyton interdigitale* (antrophilic + zoophilic) I, II, III, III*, IV, M probe
GAGATGCGCGGAAACCTC SEQ ID NO: 17:
*Trichophyton benhamiae* (yellow) probe
GTGTAGGCAATGATTTTGGGCCTACAT -continued

SEQ ID NO: 18:
*Trichophyton benhamiae*
(white) probe
TGCAGTGCGGTGTGACAGCATTTGG

SEQ ID NO: 19:
*Trichophyton benhamiae*
(african) probe
CAGTGCGGCTTGACAACAC

SEQ ID NO: 20:
*Trichophyton concentricum*
probe
AAAGTTGGGGCAGGGGAAGA

SEQ ID NO: 21:
*Trichophyton erinacei* probe
TTGCAGTGTGGGTTAGCAACATTTG

SEQ ID NO: 22:
Consensus sequence
cacnnnnntaaccntacccnnnntccnngnngnnnggnnnnnnancnnntggattatggnntnnttcgtggantanggtnnnna nncgatcntgnnnatggcactnntnggtnnnntgnnncanntnccaaaagnngnngcagggnnnnaccnnnttnnnnnntggn anggtgtaggcaatnnttntgnnncnncatcgnngangnnnatcgnngnagna SEQ ID NO: 23:
Primer
ctggccatggcacttattgg SEQ ID NO: 24:
Probe
gatgtaggcccaaaatcattgcctacac SEQ ID NO: 25:
Probe
ctgccccaacttttggcaactg SEQ ID NO: 26:
Probe
taggcaatgattttgggccta SEQ ID NO: 27:
Probe
catcggcgaggaccatcgga SEQ ID NO: 28:
Probe
gcaatggttctgggcctacatc SEQ ID NO: 29:
Sequence from *T. rubrum*
cttttgtgagagagtccagttgcacgcctgtaaccgtacccgaagtccttgcagtacggtttggccacatttggattatggagt gcttcgtggactatagtggtgacacgatcctgaccatggcacttattggtccagtggggtagttgccaaaagggccgcagggg aagaccgcattctgaattggaagagtgtaggcaatggttctgggcctacatcggtgatgcatatcggagcagtgc SEQ ID NO: 30:
Sequence from *T. verrucosum*
ctattgggagggagtccagttgcactcctgtaaccgtacccatggtccttggcgtgcggggacataacatttggattatgggct ccttcgtggattacggtcccaacacgatcctgacgatggcactccttgttgacgtggggcagttgccaaaagggggggcagggg aagaccgaattcatagatggaagggtgtaggcaatggttctgggactgcatcggcgatatttatcggagcagaac

EXAMPLES

The following examples demonstrate that different pathogen strains may be distinguished using the teachings according to the present invention.

Example 1

Design of Primers and Probes

For the identification of *T. tonsurans* in a sample, the metalloprotease gene was chosen as a useful target region. Based on the comparison of oligonucleotide sequences, a set of primers (forward primer 5' cy3-GGGAGGGA-GACTAGTTG 3' (SEQ ID NO: 10), reverse primer 5' cy3-AATTTTTCGCCGCCAAG 3"(SEQ ID NO: 12)) and a species-specific probe (5' C6-Amino-linker-GATCCTTGGCGTACGGATGCATA 3"(SEQ ID NO: 14)) for the detection of *Trichophyton tonsurans* were designed. The designed probes were checked for internal repeats, secondary structure, melting temperature and GC content.

DNA Microarray

The designed probe for *T. tonsurans* and some controls were spotted with the sciFLEXARRAYER S11 (Scienion AG, Germany) on a solid carrier material as microscopically small spots located at defined positions.

DNA Extraction from Dermatophyte Cultures

Cultures were performed on dermatophyte test medium agar (SIFIN, Germany, TN 2102). The DNA from cultured *T. tonsurans* (CBS 483.76), *T. interdigitale* anthrophilic/zoophilic (2235, Pelo1) and *T. equinum* (CBS 127.97) was extracted using the OmniPrep™ for Fungus kit (G-Biosciences, USA, no. 786-399) according to the manufacturer's instructions and identified at species level by internal transcribe spacer (ITS) sequencing.

PCR

Each PCR reaction was performed in a volume of 20 µl by the addition of 5 µl DNA extract (5 ng/µl) from *Trichophyton tonsurans, Trichophyton interdigitale* (anthrophilic), *Trichophyton interdigitale* (zoophilic) or *Trichophyton equinum*. Each reaction contained of 1× Green GoTaq® Flexi Buffer (Promega, USA, X9801), 2.5 mM MgCl2 (Promega, USA, X9801), 0.4 mM each dNTPs (25 mM each) (Bioline, Germany, BIO-39029), 0.75 U GoTaq® Flexi DNA Polymerase (5 U/µl) (Promega, USA, M830), 0.5 µM forward primer and 0.5 µM reverse primer (Metabion, Germany). The amplification was performed in a ABI 2720 thermal cycler (Applied Biosystems, USA, no. 4359659) and consisted of a pre-melt step for 3 min at 96° C. and 35 cycles of 15 s at 96° C. (melt), 15 s at 52° C. (annealing), 40 s at 72° C. (extend) and finished with a 1 min hold at 72° C.

Hybridization

The amplicons resulting from the PCR reaction comprised a fluorescent dye attached to the 5' end of the forward and/or reverse primers, which makes the amplicon detectable by a microarray scanner (EUROIMMUN AG, EUROArrayScanner, YG 0602-0101) if the PCR products bind to the complementary probe on the microarray. For the hybridization step, 25 µl PCR products were mixed with 65 µl hybridization buffer A (EUROIMMUN AG, hybridization buffer A, ZM0101-0108). 65 µl of this mixture was hybridized to the microarray using the EUROIMMUN titerplane technique (EUROIMMUN AG, titerplane+hybridization station, ZM 9999-0105+YG 0615-0101). After one hour of incubation at 55° C., the EUROArray slides were washed with special buffer solutions, according to the manufacturer's protocol, to remove non-specific bonding sequences (EUROIMMUN AG, wash reagent 1+2, ZM 0121-0050+ZM0122-0012). After washing, the slides were dried with compressed air and only strongly paired strands remained hybridized. A hybridization with labeled PCR product generated a signal which was detected via microarray scanner.

Readout and Evaluation

Final data readout and its evaluation were done using the EUROArrayScanner and EUROArrayScan software (EUROIMMUN AG, EUROArrayScan software, YG 0901-0101). Captured microarrays with hybridized PCR products from *Trichophyton tonsurans, Trichophyton interdigitale* (anthrophilic), *Trichophyton interdigitale* (zoophilic) and *Trichophyton equinum* templates are shown in FIGS. 2A-2D.

The specific probe for *Trichophyton tonsurans* is highlighted by a white circle and the dotted encircled spots are controls needed from the software to set the grid. Only the PCR products from the *Trichophyton tonsurans* template (C) hybridized to the specific probe (6a, 6b) and showed fluorescent signals, which are absent when DNA from any of the other trains was used.

This demonstrates that the inventive method may be used to distinguish *Trichophyton* strains associated with a skin, hair and nail disease.

Example 2

Material and Methods

DNA microarrays consist of DNA molecules (probes) that differ from one another by their DNA sequence. When the DNA of an organism contains segments that match to these defined probes at the microarray, the complementary DNA regions bind together (hybridize). Due to fluorescence labeled primers that are used in the polymerase chain reaction (PCR), a positive hybridization between probe and amplified target sequence can be detected via microarray scanner. An evaluated positive signal means that the target sequence could be detected. In this example the detection of the dermatophyte *Trichophyton* benhamiae (yellow) and *Trichophyton concentricum* via DNA microarray will be shown. For the verification of probe specificity the most closely related species *Trichophyton* benhamiae (white) and *Trichophyton* benhamiae (african) were also included in the analysis. The used method based on the EUROIMMUN DNA microarray platform.

Design of Primers and Probes

For the identification of *Trichophyton* benhamiae (yellow) and *Trichophyton concentricum* in a sample the metalloprotease gene was chosen as a useful target region. Based on the comparison of oligonucleotide sequences a set of primers (forward primer 5' cy3-CTGGCCATGGCACTTATTGG 3' (SEQ ID NO: 23), reverse primer 5' cy3-TGGCTCTGT-TACGTG 3' (SEQ ID NO: 13)) and species-specific probes for the detection of *Trichophyton* benhamiae (yellow) (5' C6-Amino-linker-GATGTAGGCCCAAAATCATTGCC-TACAC 3"(SEQ ID NO: 24)) and *Trichophyton concentricum* (5' C6-Amino-linker-CTGCCC-CAACTTTTGGCAACTG 3' (SEQ ID NO: 25)) were designed. The designed probes were checked for internal repeats, secondary structure, melting temperature (Tm) and GC content.

DNA Microarray

The designed probe for *Trichophyton* benhamiae (yellow), *Trichophyton concentricum* and some controls were spotted with the sciFLEXARRAYER S11 (Scienion AG, Germany) to a solid carrier material as microscopically small spots located at defined positions.

DNA Extraction from Dermatophyte Cultures

Cultures were performed on dermatophyte test medium agar (SIFIN, Germany, TN 2102). The DNA from cultured *Trichophyton* benhamiae (yellow) (CBS 623.66), *Trichophyton* benhamiae (white) (CBS 280.83), *Trichophyton* benhamiae (african) (CBS 808.72) and *Trichophyton concentricum* (CBS 563.83) was extracted using the OmniPrep™ for Fungus kit (G-Biosciences, USA, no. 786-399) according to the manufacturer's instructions and identified at species level by internal transcribe spacer (ITS) sequencing.

PCR

Each PCR reaction was performed in a volume of 20 µl by the addition of 5 µl DNA extract (5 ng/µl) from *Trichophyton* benhamiae (yellow), *Trichophyton* benhamiae (white), *Trichophyton* benhamiae (african) and *Trichophyton concentricum*. Each reaction contained of 1× Green GoTaq® Flexi Buffer (Promega, USA, X9801), 2.5 mM MgCl2 (Promega, USA, X9801), 0.4 mM each dNTPs (25 mM each) (Bioline, Germany, BIO-39029), 0.75 U GoTaq® Flexi DNA Polymerase (5 U/µl) (Promega, USA, M830), 0.8 µM forward primer and 0.4 µM reverse primer (Metabion, Germany). The amplification was performed in a ABI 2720 thermal cycler (Applied Biosystems, USA, no. 4359659) and consisted of a pre-melt step for 3 min at 96° C. and 35 cycles of 15 s at 96° C. (melt), 15 s at 52° C. (annealing), 40 s at 72° C. (extend) and finished with a 1 min hold at 72° C.

Hybridization

The resulting PCR products were labelled with a fluorescent dye, which enables them to be detected by the microarray scanner (EUROIMMUN AG, EUROArrayScanner, YG 0602-0101) if the PCR products bind to the complementary probe on the microarray. For the hybridization step 25 µl PCR products were mixed with 65 µl hybridization buffer A (EUROIMMUN AG, hybridization buffer A, ZM0101-0108). 65 µl of this mixture was hybridized to the microarray using the EUROIMMUN titerplane technique (EUROIMMUN AG, titerplane+hybridization station, ZM 9999-0105+ YG 0615-0101). After one hour of incubation at 55° C. the EUROArray slides were washed with special buffer solutions, according to the manufacturer's protocol, to remove non-specific bonding sequences (EUROIMMUN AG, wash reagent 1+2, ZM 0121-0050+ZM0122-0012). After washing the slides were dried with compressed air and only strongly paired strands remained hybridized. Hybridization with labeled PCR product generated a signal which was detected via microarray scanner.

Readout and Evaluation

Final data readout and its evaluation were done using the EUROArrayScanner and EUROArrayScan software (EUROIMMUN AG, EUROArrayScan software, YG 0901-0101). Captured microarrays with hybridized PCR products from *Trichophyton* benhamiae (yellow), *Trichophyton* benhamiae (white), *Trichophyton* benhamiae (african) and *Trichophyton concentricum* templates are shown in FIGS. 3A-3D. Strains were identified as being a *Trichophyton* benhamiae (yellow) or *Trichopyhton concentricum* when the specific probes (white circle in FIGS. 3A-3D) hybridized with cy3-labeled PCR products and the controls at the microarray also showed fluorescent signals due to a hybridization between labeled oligonucleotides in the hybridization buffer and probe sequences in the corner of the array.

Example 3

Material and Methods

DNA microarrays consist of DNA molecules (probes) that differ from one another by their DNA sequence. When the DNA of an organism contains segments that match to these defined probes at the microarray, the complementary DNA regions bind together (hybridize). Due to fluorescence labeled primers that are used in the polymerase chain reaction (PCR), a positive hybridization between probe and amplified target sequence can be detected via microarray scanner. An evaluated positive signal means that the target sequence could be detected. In this example the detection of the dermatophyte *Trichophyton* benhamiae (yellow) and *Trichophyton* benhamiae (white/african) via DNA microarray will be shown. The used method based on the EUROIMMUN DNA microarray platform.

Design of Primers and Probes

For the identification of *Trichophyton* benhamiae (yellow) or *Trichophyton* benhamiae (white/african) in a sample the metalloprotease gene was chosen as a useful target region. Based on the comparison of oligonucleotide sequences a set of primers (forward primer 5" cy3-CTGGCCATGGCACT-TATTGG 3" (SEQ ID NO: 23), reverse primer 5" cy3-TGGCTCTGTTACGTG 3" (SEQ ID NO: 13)) and species-specific probes for the detection of *Trichophyton* benhamiae (yellow) (5" C6-Amino-linker-TAGGCAATGAT-TTTGGGCCTA (SEQ ID NO: 26)) and *Trichophyton* benhamiae (white/african) (5" C6-Amino-linker-CATCGGCGAGGACCATCGGA 3"(SEQ ID NO: 27)) were designed. The designed probes were checked for internal repeats, secondary structure, melting temperature (Tm) and GC content.

DNA Microarray

The designed probe for *Trichophyton* benhamiae (yellow), *Trichophyton* benhamiae (white/african) and some controls were spotted with the sciFLEXARRAYER S11 (Scienion AG, Germany) to a solid carrier material as microscopically small spots located at defined positions.

DNA Extraction from Dermatophyte Cultures

Cultures were performed on dermatophyte test medium agar (SIFIN, Germany, TN 2102). The DNA from cultured *Trichophyton* benhamiae (yellow) (CBS 623.66), *Trichophyton* benhamiae (white) (CBS 280.83) and *Trichophyton* benhamiae (african) (CBS 808.72) was extracted using the OmniPrep™ for Fungus kit (G-Biosciences, USA, no. 786-399) according to the manufacturer's instructions and identified at species level by internal transcribe spacer (ITS) sequencing.

PCR

Each PCR reaction was performed in a volume of 20 µl by the addition of 5 µl DNA extract (5 ng/µl) from *Trichophyton* benhamiae (yellow), *Trichophyton* benhamiae (white) and *Trichophyton* benhamiae (african). Each reaction contained of 1× Green GoTaq® Flexi Buffer (Promega, USA, X9801), 2.5 mM MgCl2 (Promega, USA, X9801), 0.4 mM each dNTPs (25 mM each) (Bioline, Germany, BIO-39029), 0.75 U GoTaq® Flexi DNA Polymerase (5 U/µl) (Promega, USA, M830), 0.4 µM forward primer and 1.6 µM reverse primer (Metabion, Germany). The amplification was performed in a ABI 2720 thermal cycler (Applied Biosystems, USA, no. 4359659) and consisted of a pre-melt step for 3 min at 96° C. and 35 cycles of 15 s at 96° C. (melt), 15 s at 52° C. (annealing), 40 s at 72° C. (extend) and finished with a 1 min hold at 72° C.

Hybridization

The resulting PCR products were labelled with a fluorescent dye, which enables them to be detected by the microarray scanner (EUROIMMUN AG, EUROArrayScanner, YG 0602-0101) if the PCR products bind to the complementary probe on the microarray. For the hybridization step 25 µl PCR products were mixed with 65 µl hybridization buffer A (EUROIMMUN AG, hybridization buffer A, ZM0101-0108). 65 µl of this mixture was hybridized to the microarray using the EUROIMMUN titerplane technique (EUROIMMUN AG, titerplane+hybridization station, ZM 9999-0105+ YG 0615-0101). After one hour of incubation at 55° C. the EUROArray slides were washed with special buffer solutions, according to the manufacturer's protocol, to remove non-specific bonding sequences (EUROIMMUN AG, wash reagent 1+2, ZM 0121-0050+ZM0122-0012). After washing the slides were dried with compressed air and only strongly paired strands remained hybridized. Hybridization with labeled PCR product generated a signal which was detected via microarray scanner.

Readout and Evaluation

Final data readout and its evaluation were done using the EUROArrayScanner and EUROArrayScan software (EUROIMMUN AG, EUROArrayScan software, YG 0901-0101). Captured microarrays with hybridized PCR products from *Trichophyton* benhamiae (yellow), *Trichophyton* benhamiae (white) and *Trichophyton* benhamiae (african) templates are shown in FIGS. 4A-4C. Strains were identified as being a *Trichophyton benhamiae* (yellow) or *Trichophyton benhamiae* (white/african) when the specific probes (white circle in FIGS. 4A-4C) hybridized with cy3-labeled PCR products and the controls at the microarray also showed fluorescent signals due to a hybridization between labeled oligonucleotides in the hybridization buffer and probe sequences in the corner of the array.

Example 4

Material and Methods

DNA microarrays consist of DNA molecules (probes) that differ from one another by their DNA sequence. When the DNA of an organism contains segments that match to these defined probes at the microarray, the complementary DNA regions bind together (hybridize). Due to fluorescence labeled primers that are used in the polymerase chain reaction (PCR), a positive hybridization between probe and amplified target sequence can be detected via microarray scanner. An evaluated positive signal means that the target sequence could be detected. In this example the detection of the dermatophyte *Trichophyton erinacei* via DNA microarray will be shown. For the verification of probe specificity the most closely related species *Trichophyton benhamiae* (white) and *Trichophyton benhamiae* (african) were also included in the analysis. The used method based on the EUROIMMUN DNA microarray platform.

Design of Primers and Probes

For the identification of *Trichophyton erinacei* in a sample the metalloprotease gene was chosen as a useful target region. Based on the comparison of oligonucleotide sequences a set of primers (forward primer 5' cy3-CTGGC-CATGGCACTTATTGG 3' (SEQ ID NO: 23), reverse primer 5' cy3-TGGCTCTGTTACGTG 3' (SEQ ID NO: 13)) and a species-specific probe for the detection of *Trichophyton erinacei* (5' C6-Amino-linker-GATGTAGGCC-CAAAATCATTGCCTACAC 3' (SEQ ID NO: 24)) was designed. The designed probe was checked for internal repeats, secondary structure, melting temperature (Tm) and GC content.

DNA Microarray

The designed probe for *Trichophyton erinacei* and some controls were spotted with the sciFLEXARRAYER S11 (Scienion AG, Germany) to a solid carrier material as microscopically small spots located at defined positions.

DNA Extraction from Dermatophyte Cultures

Cultures were performed on dermatophyte test medium agar (SIFIN, Germany, TN 2102). The DNA from cultured *Trichophyton erinacei* (CBS 677.86), *Trichophyton benhamiae* (white) (CBS 280.83) and *Trichophyton benhamiae* (african) (CBS 808.72) was extracted using the OmniPrep™ for Fungus kit (G-Biosciences, USA, no. 786-399) according to the manufacturer's instructions and identified at species level by internal transcribe spacer (ITS) sequencing.

PCR

Each PCR reaction was performed in a volume of 20 µl by the addition of 5 µl DNA extract (5 ng/µl) from *Trichophyton erinacei*, *Trichophyton benhamiae* (white) and *Trichophyton benhamiae* (african). Each reaction contained of 1× Green GoTaq® Flexi Buffer (Promega, USA, X9801), 2.5 mM MgCl2 (Promega, USA, X9801), 0.4 mM each dNTPs (25 mM each) (Bioline, Germany, BIO-39029), 0.75 U GoTaq® Flexi DNA Polymerase (5 U/µl) (Promega, USA, M830), 0.5 µM forward primer and 0.5 µM reverse primer (Metabion, Germany). The amplification was performed in a ABI 2720 thermal cycler (Applied Biosystems, USA, no. 4359659) and consisted of a pre-melt step for 3 min at 96° C. and 35 cycles of 15 s at 96° C. (melt), 15 s at 52° C. (annealing), 40 s at 72° C. (extend) and finished with a 1 min hold at 72° C.

Hybridization

The resulting PCR products were labelled with a fluorescent dye, which enables them to be detected by the microarray scanner (EUROIMMUN AG, EUROArrayScanner, YG 0602-0101) if the PCR products bind to the complementary probe on the microarray. For the hybridization step 25 µl PCR products were mixed with 65 µl hybridization buffer A (EUROIMMUN AG, hybridization buffer A, ZM0101-0108). 65 µl of this mixture was hybridized to the microarray using the EUROIMMUN titerplane technique (EUROIMMUN AG, titerplane+hybridization station, ZM 9999-0105+YG 0615-0101). After one hour of incubation at 55° C. the EUROArray slides were washed with special buffer solutions, according to the manufacturer's protocol, to remove non-specific bonding sequences (EUROIMMUN AG, wash reagent 1+2, ZM 0121-0050+ZM0122-0012). After washing the slides were dried with compressed air and only strongly paired strands remained hybridized. Hybridization with labeled PCR product generated a signal which was detected via microarray scanner.

Readout and Evaluation

Figure 5A:
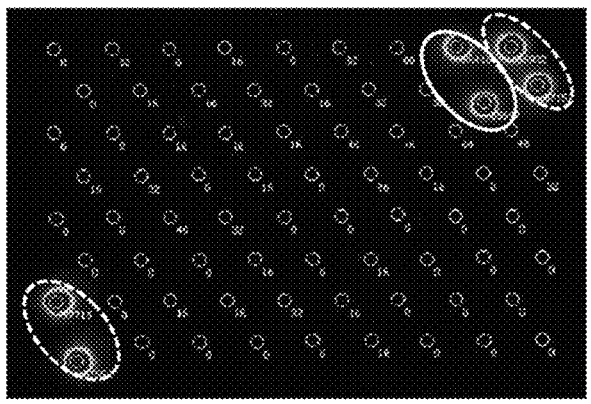
FIGS. 5A-5C shows captured microarrays with hybridized PCR products from *Trichophyton erinacei* (A), *Trichophyton* benhamiae (white) (B) and *Trichophyton* benhamiae (african) (C) templates. The specific probes for *Trichophyton erinacei* is highlighted by a white circle and the dotted encircled spots are controls needed from the software to set the grid. Only the PCR product from the *Trichophyton erinacei* (A) template hybridized to the specific probe and showed fluorescent signals.
Figure 5B:
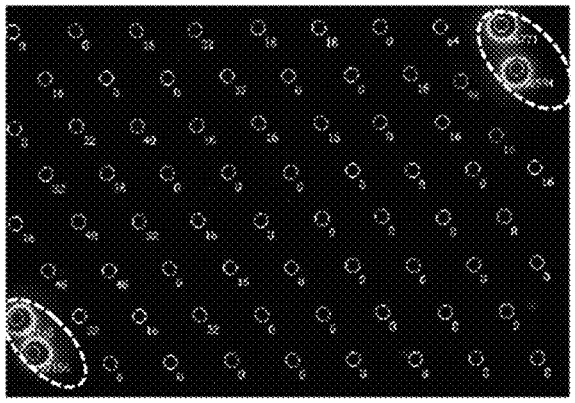
Figure 5C:
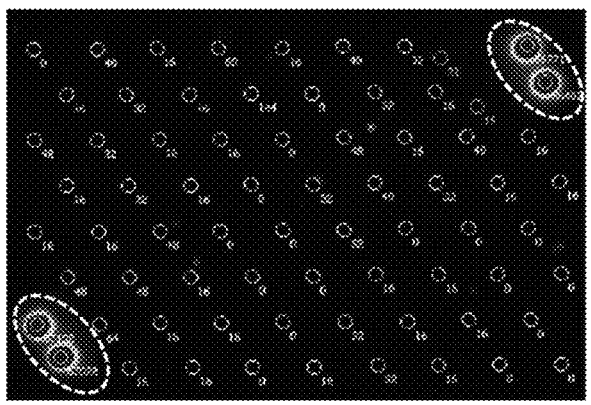

Final data readout and its evaluation were done using the EUROArrayScanner and EUROArrayScan software (EUROIMMUN AG, EUROArrayScan software, YG 0901-0101). Captured microarrays with hybridized PCR products from *Trichophyton erinacei*, *Trichophyton benhamiae* (white) and *Trichophyton benhamiae* (african) templates are shown in FIGS. 5A-5C. Strains were identified as being a *Trichophyton erinacei* when the specific probe (white circle in FIGS. 5A-5C) hybridized with cy3-labeled PCR products and the controls at the microarray also showed fluorescent signals due to a hybridization between labeled oligonucleotides in the hybridization buffer and probe sequences in the corner of the array.

Example 5

Material and Methods

DNA microarrays consist of DNA molecules (probes) that differ from one another by their DNA sequence. When the DNA of an organism contains segments that match to these defined probes at the microarray, the complementary DNA regions bind together (hybridize). Due to fluorescence labeled primers that are used in the polymerase chain reaction (PCR), a positive hybridization between probe and amplified target sequence can be detected via microarray scanner. An evaluated positive signal means that the target sequence could be detected. In this example the detection of the dermatophyte *Trichophyton benhamiae* (white), *Trichophyton benhamiae* (yellow) and *Trichophyton concentricum* via DNA microarray will be shown. The used method based on the EUROIMMUN DNA microarray platform.

Design of Primers and Probes

For the identification of *Trichophyton benhamiae* (white), *Trichophyton benhamiae* (yellow) and *Trichophyton concentricum* in a sample the metalloprotease gene was chosen as a useful target region. Based on the comparison of oligonucleotide sequences a set of primers (forward primer 5' cy3-GCATTTCCCATGGCT 3' (SEQ ID NO: 11), reverse primer 5' cy3-TGGCTCTGTTACGTG 3' (SEQ ID NO: 13)) and species-specific probes for the detection of *Trichophyton benhamiae* (white/african) (5' C6-Amino-linker-CATCGGCGAGGACCATCGGA 3' (SEQ ID NO: 27)),

*Trichophyton benhamiae* (yellow) (5' C6-Amino-linker-TAGGCAATGATTTTGGGCCTA 3' (SEQ ID NO: 26)) and *Trichophyton concentricum* (5' C6-Amino-linker-GCAATGGTTCTGGGCCTACATC 3"(SEQ ID NO: 28)) were designed. The designed probes were checked for internal repeats, secondary structure, melting temperature (Tm) and GC content.

DNA Microarray

The designed probes for *Trichophyton benhamiae* (white), *Trichophyton benhamiae* (yellow), *Trichophyton concentricum* and some controls were spotted with the sciFLEXARRAYER S11 (Scienion AG, Germany) to a solid carrier material as microscopically small spots located at defined positions.

DNA Extraction from Dermatophyte Cultures

Cultures were performed on dermatophyte test medium agar (SIFIN, Germany, TN 2102). The DNA from cultured *Trichophyton benhamiae* (african) (CBS 808.72), *Trichophyton benhamiae* (yellow) (CBS 623.66) and *Trichophyton concentricum* (CBS 563.83) was extracted using the OmniPrep™ for Fungus kit (G-Biosciences, USA, no. 786-399) according to the manufacturer's instructions and identified at species level by internal transcribe spacer (ITS) sequencing.

PCR

Each PCR reaction was performed in a volume of 20 µl by the addition of 5 µl DNA extract (5 ng/µl) from *Trichophyton benhamiae* (white), *Trichophyton benhamiae* (yellow), *Trichophyton concentricum*. Each reaction contained of 1× Green GoTaq® Flexi Buffer (Promega, USA, X9801), 2.5 mM MgCl2 (Promega, USA, X9801), 0.4 mM each dNTPs (25 mM each) (Bioline, Germany, BIO-39029), 0.75 U GoTaq® Flexi DNA Polymerase (5 U/µl) (Promega, USA, M830), 1.0 µM forward primer and 1.0 µM reverse primer (Metabion, Germany). The amplification was performed in a ABI 2720 thermal cycler (Applied Biosystems, USA, no. 4359659) and consisted of a pre-melt step for 3 min at 96° C. and 35 cycles of 15 s at 96° C. (melt), 15 s at 52° C. (annealing), 40 s at 72° C. (extend) and finished with a 1 min hold at 72° C.

Hybridization

The resulting PCR products were labelled with a fluorescent dye, which enables them to be detected by the microarray scanner (EUROIMMUN AG, EUROArrayScanner, YG 0602-0101) if the PCR products bind to the complementary probe on the microarray. For the hybridization step 25 µl PCR products were mixed with 65 µl hybridization buffer A (EUROIMMUN AG, hybridization buffer A, ZM0101-0108). 65 µl of this mixture was hybridized to the microarray using the EUROIMMUN titerplane technique (EUROIMMUN AG, titerplane+hybridization station, ZM 9999-0105+ YG 0615-0101). After one hour of incubation at 55° C. the EUROArray slides were washed with special buffer solutions, according to the manufacturer's protocol, to remove non-specific bonding sequences (EUROIMMUN AG, wash reagent 1+2, ZM 0121-0050+ZM0122-0012). After washing the slides were dried with compressed air and only strongly paired strands remained hybridized. A hybridization with labeled PCR product generated a signal which was detected via microarray scanner.

Readout and Evaluation

Figure 6A:
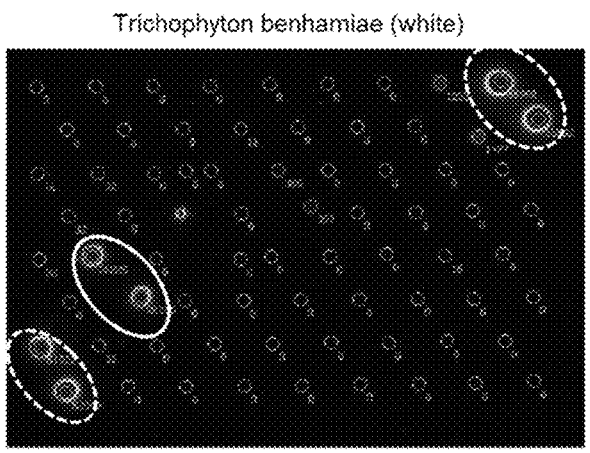
FIGS. 6A-6C shows captured microarrays with hybridized PCR products from *Trichophyton* benhamiae (white) (A), *Trichophyton* benhamiae (yellow) (B) and *Trichophyton concentricum* (C) templates. The specific probes for *Trichophyton* benhamiae (white/african), *Trichophyton* benhamiae (yellow) and *Trichophyton concentricum* are highlighted by a white circle and the dotted encircled spots are controls needed from the software to set the grid. Only the PCR products from the *Trichophyton* benhamiae (white), *Trichophyton* benhamiae (yellow) and *Trichophyton concentricum* template hybridized to the specific probe and showed fluorescent signals.
Figure 6B:
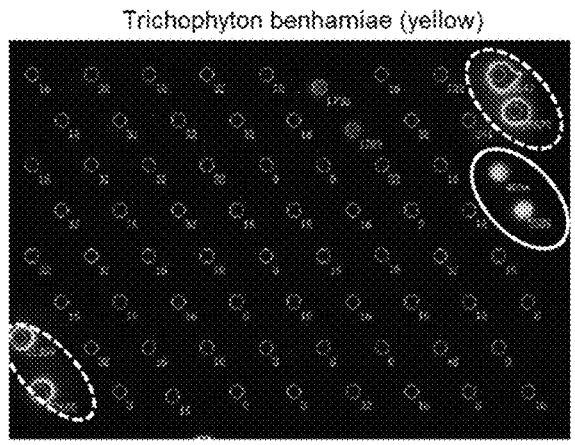
Figure 6C:
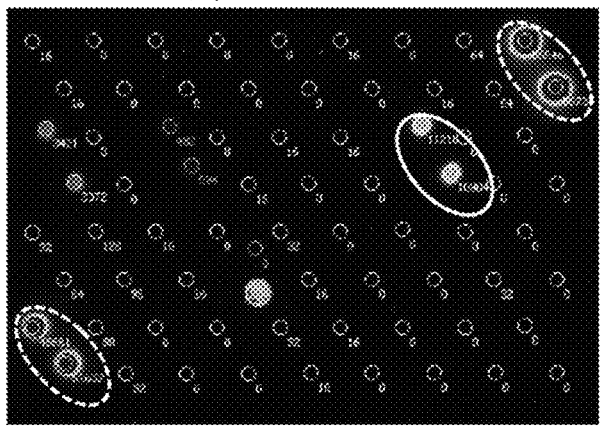

Final data readout and its evaluation were done using the EUROArrayScanner and EUROArrayScan software (EUROIMMUN AG, EUROArrayScan software, YG 0901-0101). Captured microarrays with hybridized PCR products from *Trichophyton benhamiae* (white), *Trichophyton benhamiae* (yellow) and *Trichophyton concentricum* templates are shown in FIGS. 6A-6C. Strains were identified as being a *Trichophyton benhamiae* (white/african), *Trichophyton benhamiae* (yellow) and *Trichophyton concentricum* when the specific probe (white circle in FIGS. 6A-6C) hybridized with cy3-labeled PCR products and the controls at the microarray also showed fluorescent signals due to a hybridization between labeled oligonucleotides in the hybridization buffer and probe sequences in the corner of the array.

The invention claimed is:

1. A primer pair, comprising:
a forward primer having a length of 14 to 30 nucleotides, being at least 90% identical to *Trichophyton* sequence over the full-length of the forward primer, and having a final base of the forward primer no more than 200 bp away from a first base of SEQ ID NO: 1 in a 5' to 3' orientation, and
a reverse primer having a length of 14 to 30 nucleotides, being at least 90% identical to *Trichophyton* sequence over the full-length of the reverse primer, and having a final base of the reverse primer is no more than 200 bp away from a final base of SEQ ID NO: 1 in the 5' to 3' orientation,
wherein each of the forward primer and the reverse primer are labeled with a label and form the primer pair, wherein the label is selected from the group consisting of a fluorescent label, a radioactive label, a colloidal gold label, and an enzymatically active label,
wherein the forward primer and reverse primer, in combination, amplify a nucleic acid comprising a sequence having at least 98% identity to the full-length of SEQ ID NO: 1 from a human pathogenic dermatophyte that causes at least one of a skin, hair, and nail infection, the human pathogenic dermatophyte belonging to a *Trichophyton* genus.

2. A nucleic acid probe, comprising:
a modified nucleic acid comprising a 5' C6-amino-linker,
wherein the modified nucleic acid is capable of hybridizing specifically to a nucleic acid sequence from a single species of a human pathogenic dermatophyte that causes at least one of a skin, hair, and nail infection, the human pathogenic dermatophyte belonging to a *Trichophyton* genus, wherein the nucleic acid sequence from the human pathogenic dermatophyte comprises at least one of the sequence that is at least 98% identical to the full-length of SEQ ID NO: 1, a strand complementary to SEQ ID NO: 1, or SEQ ID NO: 1 in a vector or cell, wherein the modified nucleic acid is at least 95% identical to at least one of the full-length of SEQ ID NO: 1, the strand complementary to SEQ ID NO: 1, or SEQ ID NO: 1 in the vector or cell, over a length of at least 15 consecutive nucleotides, and wherein the length of the nucleic acid probe is no more than 200 nucleotides.

3. The nucleic acid amplified from the human pathogenic dermatophyte by the primer pair according to claim 1, wherein the nucleic acid comprises the label, wherein the nucleic acid has at least 98% identity to the full-length of SEQ ID NO: 1, and wherein the nucleic acid is amplified from the human pathogenic dermatophyte belonging to a *Trichophyton* genus.

4. A carrier comprising the nucleic acid probe according to claim 2.

5. The carrier according to claim 4, wherein the carrier is a silane coated microarray plate made from a material selected from the group consisting of a glass material, a plastic material, or a silicon material.

6. A method, comprising:
a) obtaining a sample of at least one of nail material, hair material, or skin material, from a patient,
b) amplifying, from the sample of the patient, a nucleic acid from a human pathogenic dermatophyte comprising at least one of the sequence that is at least 98% identical to the full-length of SEQ ID NO: 1, a strand complementary to SEQ ID NO: 1, or SEQ ID NO: 1 in a cell, the human pathogenic dermatophyte belonging to a *Trichophyton* genus, using a primer pair, thereby generating an amplicon, wherein the primer pair comprises:
a forward primer having a length of 14 to 30 nucleotides, being at least 90% identical to *Trichophyton* sequence over the full-length of the forward primer, and having a final base of the forward primer no more than 200 bp away from a first base of SEQ ID NO: 1 in a 5' to 3' orientation, and
a reverse primer having a length of 14 to 30 nucleotides, being at least 90% identical to *Trichophyton* sequence over the full-length of the reverse primer, and having a final base of the reverse primer no more than 200 bp away from a final base of SEQ ID NO: 1 in the 5' to 3' orientation,
wherein each of the forward primer and the reverse primer are labeled with a label and form the primer pair, wherein the label is selected from the group consisting of a fluorescent label, a radioactive label, a colloidal gold label, and an enzymatically active label.

7. The method according to claim 6, further comprising:
c) detecting the amplicon.

8. The method according to claim 7, wherein the amplicon is detected by fluorescence, radioactivity, colloidal gold, or chemiluminescence.

9. A kit for the diagnosis of at least one of a skin, hair, and nail infection caused by a human pathogenic dermatophyte, comprising:
instructions that detail how to use the kit to diagnose at least one of a skin, hair, and nail infection,
the primer pair according to claim 1, wherein the primer pair comprises the label,
a nucleic acid probe capable of hybridizing specifically to a nucleic acid sequence from the human pathogenic dermatophyte, wherein the nucleic acid probe comprises:
a modified nucleic acid comprising a 5' C6-amino-linker,
wherein the nucleic acid sequence from the human pathogenic dermatophyte comprises at least one of the sequence that is at least 98% identical to the full-length of SEQ ID NO: 1, a strand complementary to SEQ ID NO: 1, or SEQ ID NO: 1 in a vector or cell,
wherein the modified nucleic acid is at least 95% identical to the full-length of SEQ ID NO: 1, the strand complementary to SEQ ID NO: 1, or SEQ ID NO: 1 in the vector or cell, over a length of at least 15 consecutive nucleotides, and
wherein the length of the nucleic acid probe is no more than 200 nucleotides, and
a carrier for immobilizing the nucleic acid probe, wherein the carrier is a silane coated microarray plate made of a material selected from the group consisting of a glass material, a plastic material, or a silicon material.

10. The primer pair according to claim 1, wherein the *Trichophyton* is selected from the group consisting of *T. tonsurans, T. equinum, T. interdigitale, T. benhamiae* (african), *T. benhamiae* (yellow), *T. concentricum*, and *T. erinacei*.

11. The nucleic acid probe according to claim 2, wherein the *Trichophyton* is selected from the group consisting of *T. tonsurans, T. equinum, T. interdigitale, T. benhamiae* (african), *T. benhamiae* (yellow), *T. concentricum*, and *T. erinacei*.

12. The carrier according to claim 4, wherein the *Trichophyton* is selected from the group consisting of *T. tonsurans, T. equinum, T. interdigitale, T. benhamiae* (african), *T. benhamiae* (yellow), *T. concentricum*, and *T. erinacei*.

13. The method according to claim 6, wherein the *Trichophyton* is selected from the group consisting of *T. tonsurans, T. equinum, T. interdigitale, T. benhamiae* (african), *T. benhamiae* (yellow), *T. concentricum*, and *T. erinacei*.

14. The kit according to claim 9, wherein the *Trichophyton* is selected from the group consisting of *T. tonsurans, T. equinum, T. interdigitale, T. benhamiae* (african), *T. benhamiae* (yellow), *T. concentricum*, and *T. erinacei*.

15. The primer pair according to claim 1, wherein
the forward primer is capable of binding to a DNA sequence from multiple species of the human dermatophyte, and/or
the reverse primer is capable of binding to the DNA sequence from multiple species of the human dermatophyte.

16. A primer pair, comprising:
a forward primer having a length of 14 to 30 nucleotides, being at least 90% identical to *Trichophyton* sequence over the full-length of the forward primer, and having a final base of the forward primer no more than 200 bp away from a first base of SEQ ID NO: 1 in a 5' to 3' orientation, and
a reverse primer having a length of 14 to 30 nucleotides, being at least 90% identical to *Trichophyton* sequence over the full-length of the reverse primer, and having a final base of the reverse primer no more than 200 bp away from a final base of SEQ ID NO: 1 in the 5' to 3' orientation,
wherein each of the forward primer and the reverse primer are labeled with a label and form the primer pair, wherein the label is selected from the group consisting of a fluorescent label, a radioactive label, a colloidal gold label, and an enzymatically active label, wherein the forward and reverse primer, in combination, amplifies a nucleic acid comprising SEQ ID NO: 1 from a human pathogenic dermatophyte that causes at least one of a skin, hair, and nail infection, the human pathogenic dermatophyte belonging to a *Trichophyton* genus.

17. A kit, for the diagnosis of at least one of a skin, hair, and nail infection caused by a human pathogenic dermatophyte, comprising:

a primer pair comprising:

a forward primer having a length of 14 to 30 nucleotides, being at least 90% identical to *Trichophyton* sequence over the full-length of the forward primer, and having a final base of the forward primer no more than 200 bp away from a first base of SEQ ID NO: 1 in a 5' to 3' orientation, a reverse primer having a length of 14 to 30 nucleotides, being at least 90% identical to *Trichophyton* sequence over the full-length of the reverse primer, and having a final base of the reverse primer no more than 200 bp away from a final base of SEQ ID NO: 1 in the 5' to 3' orientation, wherein each of the forward primer and the reverse primer are labeled with a label and form the primer pair, wherein the label is selected from the group consisting of a fluorescent label, a radioactive label, a colloidal gold label, and an enzymatically active label, wherein the forward primer and reverse primer, in combination, amplify a nucleic acid comprising SEQ ID NO: 1 from the human pathogenic dermatophyte belonging to a *Trichophyton* genus, and a modified nucleic acid probe comprising a 5' C6-amino-linker and capable of hybridizing specifically to the nucleic acid amplified by the forward primer and the reverse primer, wherein the modified nucleic acid is at least 98% identical to at least one of SEQ ID NO: 1, the strand complementary to SEQ ID NO: 1, or SEQ ID NO: 1 in the vector or cell, over a length of at least 15 consecutive nucleotides, wherein the length of the nucleic acid probe is no more than 200 nucleotides, wherein the modified nucleic acid probe is specific to a species of the human pathogenic dermatophyte belonging to the *Trichophyton* genus.

18. A modified nucleic acid amplified from a human pathogenic dermatophyte by a primer pair, comprising:

a nucleic acid comprising at least 98% identity to the full-length of SEQ ID NO: 1 from the human pathogenic dermatophyte belonging to a *Trichophyton* genus that causes at least one of a skin, hair, and nail infection;

wherein the nucleic acid is labeled with a label to form the modified nucleic acid, wherein the label is selected from the group consisting of a fluorescent label, a radioactive label, a colloidal gold label, and an enzymatically active label; and the primer pair comprising:

a forward primer having a length of 14 to 30 nucleotides, being at least 90% identical to *Trichophyton* sequence over the full-length of the forward primer, and having a final base of the forward primer no more than 200 bp away from a first base of SEQ ID NO: 1 in a 5' to 3' orientation; and a reverse primer having a length of 14 to 30 nucleotides, being at least 90% identical to *Trichophyton* sequence over the full-length of the reverse primer, and having a final base of the reverse primer is no more than 200 bp away from a final base of SEQ ID NO: 1 in the 5' to 3' orientation.

* * * * *